United States Patent
Salzer et al.

(10) Patent No.: US 9,248,128 B2
(45) Date of Patent: Feb. 2, 2016

(54) METHOD FOR ENHANCING REMYELINATION USING GLI1 INHIBITORS

(71) Applicant: NEW YORK UNIVERSITY, New York, NY (US)

(72) Inventors: James L. Salzer, New York, NY (US); Jayshree Samanta, New York, NY (US); Gordon J. Fishell, Larchmont, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 14/374,703

(22) PCT Filed: Jan. 25, 2013

(86) PCT No.: PCT/US2013/023177
§ 371 (c)(1),
(2) Date: Jul. 25, 2014

(87) PCT Pub. No.: WO2013/112859
PCT Pub. Date: Aug. 1, 2013

(65) Prior Publication Data
US 2015/0011610 A1    Jan. 8, 2015

Related U.S. Application Data

(60) Provisional application No. 61/591,745, filed on Jan. 27, 2012, provisional application No. 61/638,988, filed on Apr. 26, 2012.

(51) Int. Cl.
| | |
|---|---|
| *A61K 48/00* | (2006.01) |
| *C07H 21/02* | (2006.01) |
| *C07H 21/04* | (2006.01) |
| *A61K 31/506* | (2006.01) |
| *A61K 31/122* | (2006.01) |
| *A61K 31/352* | (2006.01) |
| *A61K 31/353* | (2006.01) |
| *A61K 31/366* | (2006.01) |
| *A61K 31/404* | (2006.01) |
| *A61K 31/435* | (2006.01) |
| *A61K 31/505* | (2006.01) |
| *A61K 31/553* | (2006.01) |
| *A61K 31/713* | (2006.01) |
| *A61K 31/16* | (2006.01) |
| *A61K 31/437* | (2006.01) |
| *A61K 31/4436* | (2006.01) |
| *A61K 45/06* | (2006.01) |
| *C12N 15/113* | (2010.01) |

(52) U.S. Cl.
CPC ............ *A61K 31/506* (2013.01); *A61K 31/122* (2013.01); *A61K 31/16* (2013.01); *A61K 31/352* (2013.01); *A61K 31/353* (2013.01); *A61K 31/366* (2013.01); *A61K 31/404* (2013.01); *A61K 31/435* (2013.01); *A61K 31/437* (2013.01); *A61K 31/4436* (2013.01); *A61K 31/505* (2013.01); *A61K 31/553* (2013.01); *A61K 31/713* (2013.01); *A61K 45/06* (2013.01); *C12N 15/113* (2013.01); *C12N 2310/14* (2013.01)

(58) Field of Classification Search
CPC .............................. C12N 15/113; A61K 48/00
See application file for complete search history.

(56) References Cited

U.S. PATENT DOCUMENTS

| | | |
|---|---|---|
| 7,666,676 B2 | 2/2010 | Lawman et al. |
| 7,709,454 B2 | 5/2010 | Altaba et al. |
| 2007/0161588 A1 | 7/2007 | Lawman et al. |
| 2007/0179091 A1 | 8/2007 | de Sauvage et al. |
| 2009/0054517 A1 | 2/2009 | Lubahn et al. |
| 2010/0143362 A1 | 6/2010 | Walmsley et al. |
| 2010/0196388 A1 | 8/2010 | Jenkins et al. |
| 2011/0015201 A1 | 1/2011 | Chen et al. |
| 2011/0183962 A1 | 7/2011 | Dorsch et al. |
| 2011/0190239 A1 | 8/2011 | Moon et al. |
| 2013/0045240 A1 | 2/2013 | Tao et al. |
| 2014/0072630 A1 | 3/2014 | Tao et al. |

FOREIGN PATENT DOCUMENTS

| | | |
|---|---|---|
| WO | WO 01/12655 | 2/2001 |
| WO | WO 2007/139492 | 12/2007 |
| WO | WO 2008/131354 | 10/2008 |
| WO | WO 2011/025838 | 3/2011 |

OTHER PUBLICATIONS

Hosoya et al. "Naturally Occurring Small-Molecule Inhibitors of Hedgehog/GLI-Mediated Transcription" ChemBioChem 2008, 9:1082-1092.

Hyman et al. "Small-molecule inhibitors reveal multiple strategies for Hedgehog pathway blockade" PNAS 2009, 106(33):14132-14137.

International Search Report dated Apr. 22, 2013, which issued during prosecution of International Application No. PCT/US2013/023177, which corresponds to the present application.

Lauth, et al. "Inhibition of GLI-mediated transcription and tumor cell growth by small-molecule antagonists" PNAS 2007, 104(20):8455-8460.

Lee et al. "A Small-Molecule Antagonist of the Hedgehog Signaling Pathway" ChemBioChem 2007, 8:1916-1919.

Mahindroo, et al. "Structure-Activity Relationships and Cancer-Cell Selective Toxicity of Novel Inhibitors of Glioma-Associated Oncogene Homologue 1 (Gli1) Mediated Transcription" Journal of Medicinal Chemistry 2009, 52:4277-4287.

(Continued)

*Primary Examiner* — Amy Bowman
(74) *Attorney, Agent, or Firm* — Troutman Sanders LLP

(57) ABSTRACT

The invention provides a method of treatment of multiple sclerosis and other neurological disorders characterized by myelin loss or myelin deficiency by inhibiting Gli1 transcription factor. In a related aspect, the invention provides a method for enhancing neuroprotection of a central nervous system (CNS) or peripheral nervous system (PNS) neuron in a subject in need thereof comprising administering to said subject an effective amount of a Gli1 inhibitor. In one embodiment, the subject has a neurological disorder characterized by myelin loss or myelin deficiency.

22 Claims, 11 Drawing Sheets

(56) References Cited

OTHER PUBLICATIONS

Menn et al. "Origin of Oligodendrocytes in the Subventricular Zone of the Adult Brain" The Journal of Neuroscience 2006, 26(30):7907-7918.
Park et al. "Mouse Gli1 mutants are viable but have defects in SHH signaling in combination with a Gli2 mutation" Development 2000, 127:1593-1605.
Peukert, et al. "Small-Molecule Inhibitors of the Hedgehog Signaling Pathway as Cancer Therapeutics" ChemMedChem 2010, 5:500-512.
Picard-Riera, et al. "Experimental autoimmune encephalomyelitis mobilizes neural progenitors from the subventricular zone to undergo oligodendrogenesis in adult mice" PNAS 2002, 99(20):13211-13216.
Samanta, et al. "Role of Sonic Hedgehog in Remyelination", poster abstract, *Keystone Symposium*: Stem cells in tissue homeostasis, health and disease, Jan. 30,-Feb. 4, 2011.
Samanta, et al. "Role of Sonic Hedgehog in Remyelination", poster abstract, NYSTEM: Science accelerating therapies, May 24-25, 2011.
Sanchez, et al. "Inhibition of prostate cancer proliferation by interference with Sonic Hedgehog-GLI1 signaling" PNAS 2004, 101(34):12561-12566.
Stecca, et al. "Melanomas require Hedgehog-GLI signaling regulated by interactions between GLI1 and the RAS-MEK/AKT pathways" PNAS 2007, 104(14):5895-5900.
Tremblay, et al. "Recent patents for Hedgehog pathway inhibitors for the treatment of malignancy" Expert Opin. Ther. Patents 2009, 19(8):1039-1056.
Weiner, et al. "Induction of Medulloblastomas in Mice by Sonic Hedgehog, Independent of Gli1 [1,2]" Cancer Research 2002, 62:6385-6389.
Written Opinion of the International Searching Authority dated Apr. 22, 2013, which issued during prosecution of International Application No. PCT/US2013/023177, which corresponds to the present application.
Hui et al. "Gli Proteins in Development and Disease" The Annual Review of Cell and Developmental Biology, 2011, 27:513-537.
Ahn et al. "Dynamic Changes in the Response of Cells to Positive Hedgehog Signaling during Mouse Limb Patterning" Cell, 2004, 118(4):505-516.
Wang et al. "Human iPSC-Derived Oligodendrocyte Progenitor Cells Can Myelinate and Rescue a Mouse Model of Congenital Hypomyelination" Cell Stem Cell, 2013, 12:252-264, doi:10.1016/j.stem.2012.12.002.
Orentas et al. "Sonic hedgehog signaling is required during the appearance of spinal cord oligodendrocyte precursors" Development, 1999, 126:2419-2429.
Nery et al. "Sonic hedgehog contributes to oligodendrocyte specification in the mammalian forebrain" Development, 2001, 128:527-540.
Tekki-Kessaris et al. "Hedgehog-dependent oligodendrocyte lineage specification in the telencephalon" Development, 2001, 128:2545-2554.
Dessaud et al. "Pattern formation in the vertebrate neural tube: a sonic hedgehog morphogen-regulated transcriptional network" Development, 2008, 135:2489-2503 doi:10.1242/dev.009324.
Cohen et al. "A theoretical framework for the regulation of Shh morphogen-controlled gene expression" Development, 2014, 141:3868-3878 doi:10.1242/dev.112573.
Ferent et al. "Sonic Hedgehog Signaling Is a Positive Oligodendrocyte Regulator during Demyelination" The Journal of Neuroscience, 2013, 33(5):1759-1772.
Fuccillio et al. "Morphogen to mitogen: the multiple roles of hedgehog signalling in vertebrate neural development" Nature Reviews Neuroscience, 2006, 7:772-783 doi:10.1038/nrn1990.
Bambakidis et al. "Transplantation of oligodendrocyte precursors and sonic hedgehog results in improved function and white matter sparing in the spinal cords of adult rats after contusion" The Spine Journal, 2004, 4:16-26.
Carney et al. "Drugging Hedgehog: signaling the pathway to Translation" BMC Biology, 2013, 11:37.
Ingham P.W. "Hedgehog signaling" Current Biology, 2008, 18(6):R238-R241.
Dennler et al. "Induction of Sonic Hedgehog Mediators by Transforming Growth Factor-B: Smad3-Dependent Activation of Gli2 and Gli1 Expression In vitro and In vivo" Cancer Research, 2007, 67(14):6981-6986.
Yoon et al. "Noncanonical Regulation of the Hedgehog Mediator Gui by c-MYC in Burkitt Lymphoma" Molecular Cancer Research, 2013, 11(6):604-615.
Aberger et al. "Canonical and Noncanonical Hedgehog/GLI Signaling in Hematological Malignancies" Vitamins and Hormones, 2012, vol. 88, pp. 25-54. doi: 10.1016/B978-0-12-394622-5.00002-X.
European Search Report issued on Oct. 14, 2015 during prosecution of European Patent Application No. 13741571.
Khalatbary et al. "Anti-Inflammatory Effect of the Epigallocatechin Gallate Following Spinal Cord Trauma in Rat" Iranian Biomedical Journal, 31-37 (Jan. 2011).
Lauth et al. "Inhibition of GLI-mediated transcription and tumor cell growth by small-molecule antagonists" Proceedings of the National Academy of Sciences, vol. 104 No. 20, 8455-8460 (May 2007).
Razeghi et al. "Archive of SID Prevention of Animal Model of Multiple Sclerosis by oral genistein, extracted from soy bean" Iranian Journal of Neurology Nutrition and Health Faculty, XP055217622 (Sep. 2009).
Suwelack et al. "Neuronal expression of the transcription factor Gli1 using the Tal a-tubulin promoter is neuroprotective in an experimental model of Parkinson's disease" XP055217660 (Jul. 2204).
Wang et al. "Epigallocatechin-3-Gallate Ameliorates Experimental Autoimmune Encephalomyelitis by Altering Balance among CD4+ T-Cell Subsets" The American Journal of Pathology, vol. 180 No. 1, 221-234 (Jan. 2012).
Wang et al. "Paradoxial dysregulation of the neural stem cell pathway sonic hedgehog-gli1 in autoimmune encephalomyelitis and multiple sclerosis" Annals of Neurology, vol. 64 No. 4, 417-427 (Oct. 2008).

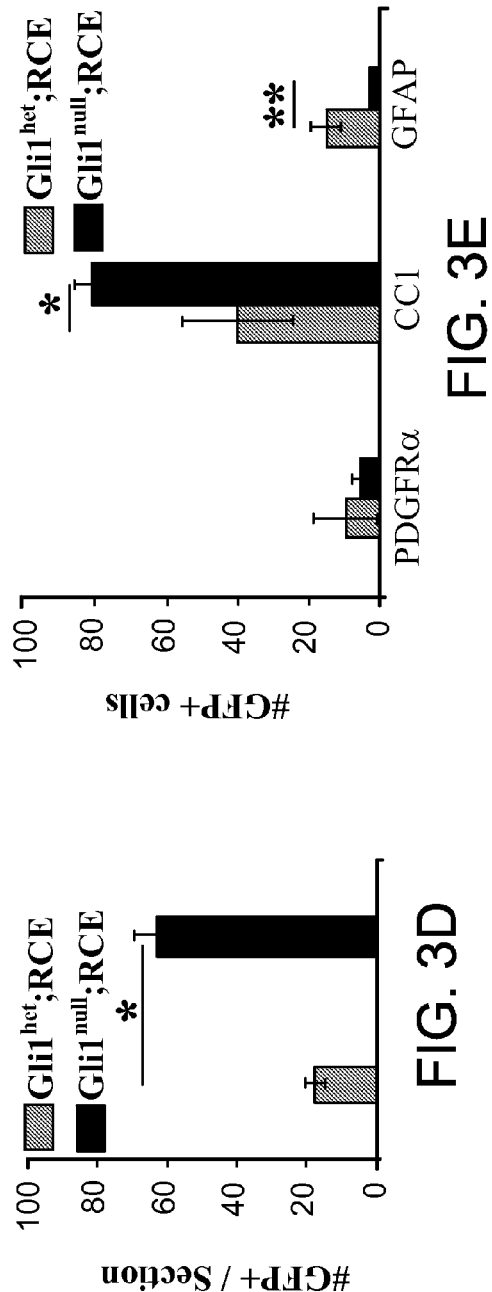
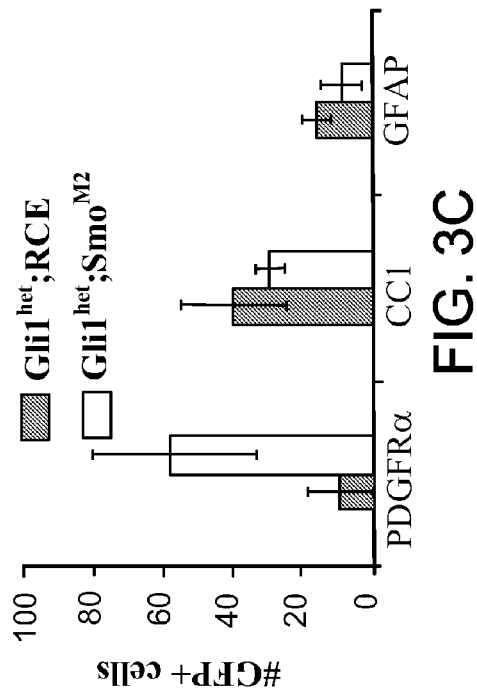
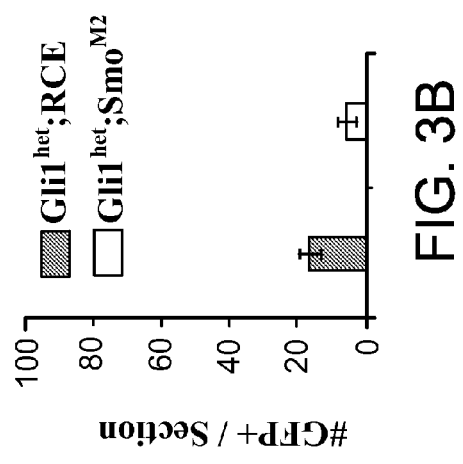
FIG. 3B
FIG. 3C
FIG. 3D
FIG. 3E

METHOD FOR ENHANCING REMYELINATION USING GLI1 INHIBITORS

CROSS REFERENCE TO RELATED APPLICATIONS

This application is a U.S. National Phase Application under 35 U.S.C. 371 of International Patent Application No. PCT/US2013/023177 filed Jan. 25, 2013 and claims the benefit of U.S. Provisional Application Ser. No. 61/591,745, filed on Jan. 27, 2012 and U.S. Provisional Application Ser. No. 61/638,988, filed on Apr. 26, 2012. The International Application was published on Aug. 1, 2013, as International Publication No. WO 2013/112859 A1 under PCT Article 21(2). The entire contents of these applications are hereby incorporated by reference.

SEQUENCE LISTING

The instant application contains a Sequence Listing which has been submitted in ASCII format via EFS-Web and is hereby incorporated by reference in its entirety. Said ASCII copy, created on Jul. 23, 2014, is named Seq27522-0200WO1.txt and is 1,453 bytes in size.

FIELD OF THE INVENTION

The invention provides a method of treatment of multiple sclerosis and other neurological disorders characterized by myelin loss or myelin deficiency by inhibiting Gli1 transcription factor.

BACKGROUND OF THE INVENTION

Myelin is a vital component of the central and peripheral nervous system. Consisting of 70% lipid and 30% protein, myelin is formed both by oligodendrocytes (OLs) in the central nervous system (CNS) and by Schwann cells in the peripheral nervous system (PNS). Working as insulation, myelin enhances the speed and integrity of nerve signal propagation down the neural axon, allowing signals to pass back and forth between the brain and the nerves of the periphery over long distances. Myelin is also neuroprotective and maintains the long-term integrity of axons. Damage to the myelin sheath from any number of causes can lead to a variety of neurological disorders with often devastating consequences.

Myelination is a multistep process in which a myelinating cell adheres to an axon, then ensheaths and wraps it, culminating with exclusion of the cytoplasm from the spiraling processes to form compact myelin. The myelin sheath is formed by the plasma membrane, or plasmalemma, of glial cells: oligodendrocytes in the CNS, Schwann cells in the PNS. The plasmalemma makes contact with the axon and then begins to wrap around it, spiral fashion, the inner mesaxon continuing to circle the axon as the plasmalemma grows and flattens, squeezing out most of the cytoplasm, until the end result is a laminated sheath consisting of multiple concentric lamellae formed of plasma membrane, each lamella consisting of a total of four lipid leaflets.

The myelin sheath is formed in segments along the length of the axon. Between segments are small unmyelinated areas known as the nodes of Ranvier. This arrangement allows for very fast neural impulse transmission via saltatory conduction, in which the active components of impulse propagation are concentrated at the nodes of Ranvier, while current flow within the axon takes place in the internodes. The integrity of the nerve conduction process can be assessed clinically through measurements of conduction velocity. When myelination fails at a particular region of axon, the spread of the action potential slows down or stops altogether, measured clinically as slowed conduction or conduction block, respectively.

Despite the importance of myelin for the rapid conduction of action potentials, little is known about the mechanism of myelination.

Disorders of myelination can produce significant impairment in sensory, motor and other types of functioning when nerve signals reach their targets slowly, asynchronously, intermittently, or not at all. Disorders of myelination are also associated with progressive loss of the axons which further contributes to neurological impairment. Disorders of myelination can be demyelinating, as a result of removal or degradation of myelin already formed; or dysmyelinating, as a result of deficient or defective myelin development or maintenance. Many disorders affect both CNS and PNS myelin. Included among the more common disorders of CNS myelination are multiple sclerosis (MS), the leukodystrophies, the Guillain Bane Syndrome, and the Charcot Marie Tooth inherited peripheral neuropathies.

Multiple sclerosis (MS) is a progressive autoimmune inflammatory and demyelinating disease of the central nervous system (CNS). The pathological hallmarks of MS are white and grey matter demyelination, inflammation, axon damage, and blood-brain barrier (BBB) disruption (Dhib-Jalbut, Neurology, vol. 68, no. 22, supplement 3, pp. S13-S54, 2007; Holmoy and Hestvik, Current Opinion in Infectious Diseases, vol. 21, no. 3, pp. 271-278, 2008; Lisak, Neurology, vol. 68, no. 22, supplement 3, pp. S5-S12, 2007, discussion S43-S54). The etiology of MS is still not clear, but MS is classically characterized by proinflammatory T helper (Th) cells, Th1 and Th17 infiltration into the CNS (Dhib-Jalbut, Neurology, vol. 68, no. 22, supplement 3, pp. S13-S54, 2007; Fletcher et al., Clinical and Experimental Immunology, vol. 162, no. 1, pp. 1-11, 2010). Whether the disease manifests in repeated episodes of inflammation or as a chronic condition, it often results in multiple scars, or plaques in the brain, that contribute to the impairment or loss of nerve function. MS, while primarily affecting young adults, can manifest in patients of any age. Symptoms of MS include, for example, impaired vision or cognitive function, numbness, weakness in extremities, tremors or spasticity, heat intolerance, speech impairment, incontinence, or impaired proprioception. Patients with MS often also present with depression.

An important but elusive goal in MS research is to enhance remyelination, i.e., the generation of new myelin sheaths to insulate and protect axons that have lost their myelin in the central nervous system (CNS). Remyelination is normally quite limited in MS (Prineas et al., 1993), particularly in the later stages of the disease when neurodegeneration, including loss of axons dominates (Franklin and French-Constant, 2008). Remyelination is expected to have the dual benefit of restoring saltatory conduction (Smith et al., 1979) to demyelinated axons and preventing axonal loss, a major source of morbidity in this disease (Bruce et al., 2010; Dubois-Dalcq et al., 2005). While there has been progress in developing therapies to prevent the immune-mediated damage in MS, progress in remyelination and neuroprotective therapies has been much more limited (Mullard, 2011). There are no currently approved therapies to promote remyelination with only one, LINGO, in clinical trials (Mullard, 2011).

Insufficient myelination in the central nervous system has also been implicated in a wide array of other neurological disorders. Among these are forms of cerebral palsy in which a congenital deficit in forebrain myelination in children with periventricular leukomalacia, contributes to neurological morbidity (Goldman et al., 2008). At the other end of the age spectrum, myelin loss and ineffective repair may contribute to the decline in cognitive function associated with senescence (Kohama et al., 2011). Therefore, effective strategies to enhance remyelination may have substantial therapeutic benefits in halting disease progression and restoring function in MS and in a wide array of neurological disorders.

Remyelination requires expansion of precursor cells, their recruitment to demyelinated axons and their subsequent differentiation into oligodendrocytes (OLs), and the formation of myelin sheaths around demyelinated axons by these newly differentiated axons (Franklin and French-Constant, 2008; Zhao et al., 2005). The precise precursor cells responsible for remyelination and the reasons why they are ineffective in the repair of demyelinated lesions in multiple sclerosis and other disorders is not known. Recent evidence suggests that there are at least two sources of remyelinating cells in the adult human and mouse brain. One is the pool of oligodendrocyte progenitor cells (OPCs) present in the parenchyma of healthy brain as well as in, and around MS lesions (Scolding, N. et al. Brain 121 (Pt 12), 2221-2228, 1998; Picard-Riera et al., Proc. Natl. Acad. Sci. U.S.A., 99, 13211-13216, 2002; Menn et al., J. Neurosci., 26, 7907-7918, 2006). OPCs, which can be identified by their expression of the NG2 chondroitin sulfate proteoglycan and platelet-derived growth factor receptor alpha (PDGFRα), respond locally to demyelination by generating oligodendrocytes. They have limited self-renewal capacity and do not migrate long distances during remyelination which may contribute to their depletion around lesion sites (Gensert and Goldman, Neuron, 19:197-203, 1997; Franklin et al., J. Neurosci. Res., 50:337-344, 1997). Another source of remyelinating oligodendrocytes are the glial fibrillary acidic protein (GFAP)-expressing multipotent stem cells (type B cells) in the subventricular zone (SVZ) (Menn et al., J. Neurosci., 26, 7907-7918, 2006). These cells can self-renew and generate all neural cell types, i.e. neurons, astrocytes and oligodendrocytes, in response to a variety of morphogenic signals including the secreted morphogen Sonic Hedgehog (Shh) (Ahn and Joyner, Nature, 437:894-897, 2005).

While generation of oligodendrocytes from the adult SVZ is normally modest (Ahn and Joyner, Nature, 437:894-897, 2005), it significantly increases in response to demyelination, including in patients with MS (Nait-Oumesmar et al., Proc. Natl. Acad. Sci. U.S.A., 104:4694-4699, 2007). The signals that drive SVZ expansion in response to demyelination are not well established.

Shh is required for the generation of oligodendrocytes during development (Nery et al., Development, 128:527-540, 2001; Tekki-Kessaris, Development, 128:2545-2554, 2001) and for the maintenance of stem cells in the adult SVZ (Ihrie et al., Neuron, 71:250-262, 2011; Balordi and Fishell, J. Neurosci., 27:14248-14259, 2007). Increased Shh expression has been found to be present in active MS lesions (Wang et al., Ann Neurol., 64:417-427, 2008). Canonical Shh signaling is mediated by interactions of the hedgehog receptor patched (Ptc) with the G-protein coupled transmembrane co-receptor smoothened (Smo). Binding of Shh to Ptc relieves its inhibition of Smo and thereby activates the Gli family of zinc finger transcription factors (Ingham and McMahon, Genes Dev., 15:3059-3087, 2001; Ruiz i Altaba et al., (2002) Nat. Rev. Cancer 2, 361-372). The GLI zinc-finger transcription factors have been suggested to be essential for the mediation of HH signals (Ingham & McMahon, (2001) Genes Dev. 15, 3059-3087; Ruiz i Altaba et al., (2002) Nat. Rev. Cancer 2, 361-372; Ruiz i Altaba et al., (2004) Cancer Lett. 204, 145-157). GLIs participate in the final step of the Hh/GLI signaling pathway, and they regulate several genes, including those that are related to cell cycle control and Hh/GLI signaling (Eichberger et al., Genomics 2006, 87, 616-632). GLI1 acts as a transcriptional activator, whereas GLI2 and GLI3 act as both activators and repressors (Matise, and Wang (2011) Curr Top Dev Biol 97, 75-117; Aza-Blanc et al., Development 2000, 127, 4293-4301). All GLIs bind to DNA through five zinc-finger domains that recognize the consensus GLI-selective sequence 5'-GACCACCCA-3' (SEQ ID NO: 1), which regulates transcription (Kinzler et al., Nature 1988, 332, 371-374; Kinzler and Vogelstein, Mol. Cell. Biol. 1990, 10, 634-642). Of the three Gli proteins, Gli1 expression is considered a sensitive readout for, and an indicator of the highest levels of Shh signaling (Ahn and Joyner, Cell, 118:505-516, 2004). However, Gli1 is apparently redundant in mouse development and tumorigenesis, and there is to date no data on the requirement for GLI1 in human cells (Park et al., (2000) Development (Cambridge, U.K.) 127, 1593-1605; Weiner et al., (2002) Cancer Res. 62, 6385-6389).

SUMMARY OF THE INVENTION

As specified in the Background Section, there is a great need in the art to develop novel therapeutics for the treatment of multiple sclerosis (MS) and other neurological disorders characterized by myelin loss or myelin deficiency. The present invention satisfies this and other needs by providing a novel method for enhancing remyelination and neuroprotection.

In one aspect, the invention provides a method for enhancing remyelination in a subject in need thereof comprising administering to said subject an effective amount of a Gli1 inhibitor. In one embodiment, the subject has a neurological disorder characterized by myelin loss or myelin deficiency.

In a related aspect, the invention provides a method for enhancing neuroprotection of a central nervous system (CNS) or peripheral nervous system (PNS) neuron in a subject in need thereof comprising administering to said subject an effective amount of a Gli1 inhibitor. In one embodiment, the subject has a neurological disorder characterized by myelin loss or myelin deficiency.

In another aspect, the invention provides a method for treating a neurological disorder characterized by myelin loss or myelin deficiency in a subject in need thereof comprising administering to said subject a therapeutically effective amount of a Gli1 inhibitor.

Non-limiting examples of neurological disorders treatable by the methods of the invention include multiple sclerosis (MS) (e.g., Relapsing/Remitting Multiple Sclerosis, Secondary Progressive Multiple Sclerosis, Progressive Relapsing Multiple Sclerosis, Primary Progressive Multiple Sclerosis, and Acute Fulminant Multiple Sclerosis), Central Pontine Myelinolysis, Acute Disseminated Encephalomyelitis, Progressive Multifocal Leukoencephalopathy, Subacute Sclerosing Panencephalitis, Post-infectious Encephalomyelitis, Chronic Inflammatory Demyelinating Polyneuropathy, Devic's Disease, Balo's Concentric Sclerosis, the leukodystrophies (e.g., Metachromatic Leukodystrophy, Krabbe disease, Adrenoleukodystrophy, Pelizaeus-Merzbacher disease, Canavan disease, Childhood Ataxia with Central Hypomyelination, Alexander disease, or Refsum disease), optic neuritis, transverse myelitis, cerebral palsy, spinal cord injury, age-associated myelin deficiency, as well as acquired and inherited neuropathies in the peripheral nervous system (e.g., Guillain-Barre Syndrome and Charcot Marie Tooth disease). In one specific embodiment, the neurological disorder is multiple sclerosis (MS).

In one specific embodiment, the Gli1 inhibitor used in the methods of the invention is GANT61. In another specific embodiment, the Gli1 inhibitor used in the methods of the invention is GANT58. In a further embodiment, the Gli1 inhibitor used in the methods of the invention is selected from the group consisting of genistein, epigallocatechin gallate (EGCG), zerumbone, zerumbone epoxide, staurosporinone, 6-hydroxystaurosporinone, arcyriaflavin C, 5,6-dihydroxyarcyriaflavin A, physalin F, and physalin B. In yet another embodiment, the Gli1 inhibitor used in the methods of the invention is selected from the group consisting of NMDA298-1, JK184, and HPI-1 through HPI-4. In another specific embodiment, the Gli1 inhibitor used in the methods of the invention is siRNA (e.g., siRNA having the sequence selected from the group consisting of GUCAUUAUCAAAU-UUCUCCTT (SEQ ID NO: 2); AGAAGAAAA-GAGUGGGCCCTT (SEQ ID NO: 3); UCCGGUGUUUU-CUUCAUCCTT (SEQ ID NO: 4); GAGAUCUUCCCUUCAUACCTT (SEQ ID NO: 5), and AACUCCACAGGCAUACAGGAU (SEQ ID NO: 6)).

In an additional embodiment, the Gli1 inhibitor useful in the methods of the invention is a compound of formula (1):

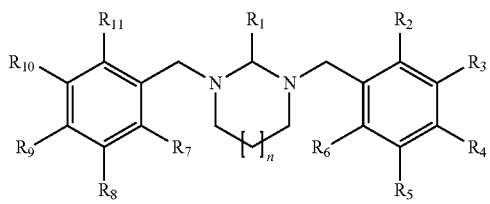
(1)

wherein
n is 0, 1, or 2;
$R_1$ is $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; and
each of $R_2$, $R_3$, $R_4$, $R_5$, $R_6$, $R_7$, $R_8$, $R_9$, $R_{10}$, and $R_{11}$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, $OR_a$, $COOR_a$, $OC(O)R_a$, $C(O)R_a$, $C(O)NR_aR_b$, or $NR_aR_b$, in which each of $R_a$ and $R_b$, independently, is H, $C_1$-$C_{10}$ alkyl, $C_3$-$C_{20}$ cycloalkyl, $C_1$-$C_{20}$ heterocycloalkyl, aryl, or heteroaryl. In one embodiment, a subset of the compounds of formula (1) are those in which n is 1. In these compounds, $R_1$ can be heteroaryl (e.g., 4-pyridyl); each of $R_2$ and $R_{11}$ can be $NR_aR_b$ (e.g., $N(CH_3)_2$), and each of $R_3$, $R_4$, $R_5$, $R_6$, $R_7$, $R_8$, $R_9$, and $R_{10}$ can be H.

In one specific embodiment, the compound of formula (1) is (Compound 1)
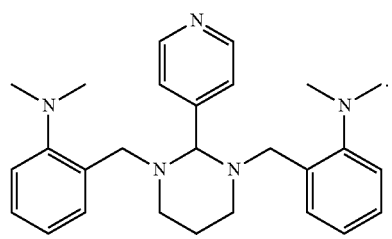

In another specific embodiment, the Gli1 inhibitor is selected from the group consisting of

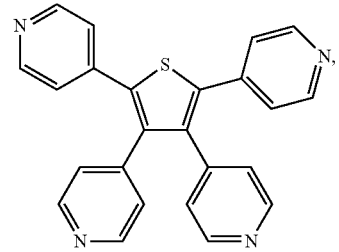

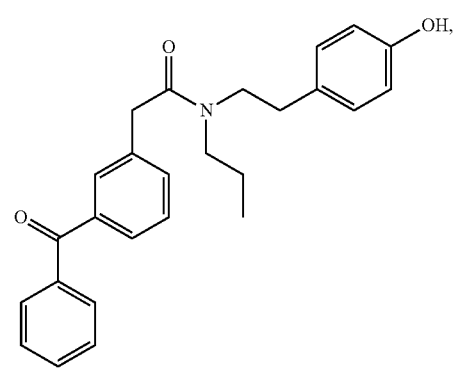

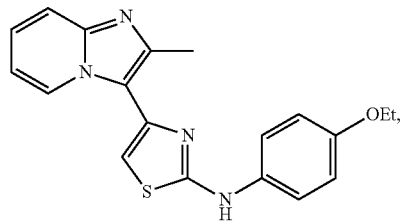

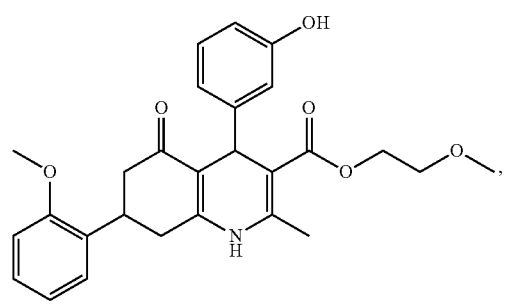

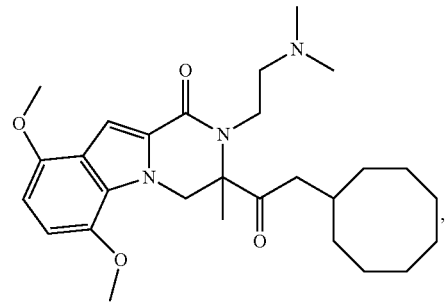

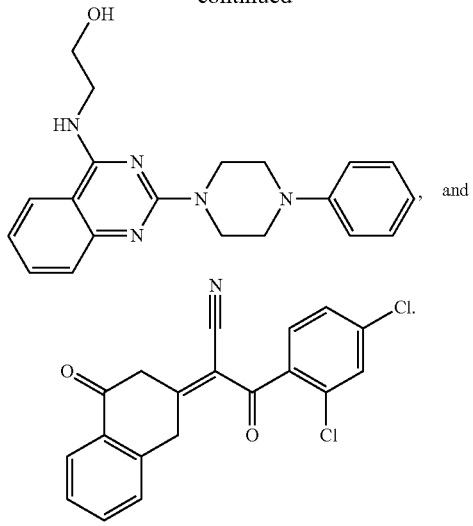

In one embodiment, the Gli1 inhibitor is formulated in a composition further comprising one or more agents which facilitate brain delivery.

In one embodiment, the Gli1 inhibitor is administered in combination with at least one additional therapeutic agent that limits demyelination. Non-limiting examples of such additional therapeutic agents include, for example, Interferon Beta 1a (Avonex), Interferon Beta 1b (Rebif), glatiramer acetate (Copaxone), mitoxantrone (Novantrone), azathiprine (Imuran), cyclophosphamide (Cytoxan or Neosar), cyclosporine (Sandimmune), ampyra, dimethyl fumarate (BG12), fingolimod, methotrexate, Cladribine (Leustatin), methylprednisone (Depo-Medrol or Solu-Medrol), prednisone (Deltasone), prednisolone (Delta-Cortef), dexamethasone (Medrol or Decadron), adreno-corticotrophic hormone (ACTH), Corticotropin (Acthar), anti-integrin specific antibodies, cytoxan, naltrexone, and the like.

In another embodiment, the Gli1 inhibitor is administered in combination with at least one additional agent that may enhance remyelination. Non-limiting examples of such agents include anti-LINGO therapies, axin/Wnt pathway inhibitors, and agonists for RXR transcription factors such as, e.g., 9-cis-retinoic acid (Fancy et al., 2011; Huang et al., 2011a; Huang et al., 2011b; Mullard, 2011).

In yet another embodiment, the Gli1 inhibitor is administered in combination with at least one agent which causes upregulation and/or increases activity of Gli2 and/or Gli3.

In a further embodiment, the Gli1 inhibitor is administered in combination with at least one agonist of smoothened (Smo) (e.g., N-Methyl-N'-(3-Pyridinylbenzyl)-N'-(3-Chlorobenzo[b]thiophene-2-carbonyl)-1,4-Diaminocyclohexane (SAG)).

BRIEF DESCRIPTION OF THE DRAWINGS

FIGS. 3A-E demonstrate enhanced recruitment and oligodendrocyte differentiation of Gli1-null stem cells following demyelination. A, Photomicrographs of sections of brains from Gli1$^{het}$;Smo$^{M2}$, Gli1$^{het}$;RCE and Gli1$^{null}$;RCE mice analyzed by immunofluorescence 2 weeks after cessation of cuprizone. GFP-labeled cells are only observed in the CC of mice receiving cuprizone (right panels). Scale bar, 50 µm. B, Quantification of the numbers of GFP-labeled cells in the Corpus Callosum (CC) shows no significant difference between the Gli1$^{het}$;Smo$^{M2}$ and Gli1$^{het}$;RCE mice. C, Percentage of GFP-labeled oligodendrocyte progenitors (PDGFRα+), mature oligodendrocytes (CC1+), and astrocytes (GFAP+) in the CC of Gli1$^{het}$;Smo$^{M2}$ and Gli1$^{het}$;RCE mice. D, Quantification of the numbers of GFP-labeled cells in the CC shows a significant increase in Gli1$^{null}$;RCE compared to Gli$^{het}$;RCE mice. E, Gli1$^{null}$;RCE mice have a greater proportion of labeled mature oligodendrocytes and reduced proportions of astrocytes than do Gli1$^{het}$;RCE mice.; n=3, Data are mean±standard deviation. Student's T test: * p=0.003; ** p=0.002. CC=Corpus Callosum.

DETAILED DESCRIPTION OF THE INVENTION

Figure 1A:
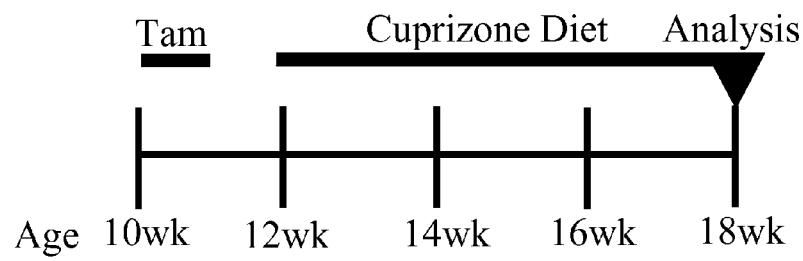
FIGS. 1A-D demonstrate that Shh-responsive cells accumulate in areas of demyelination. A, Schematic of the experimental time course for the cuprizone model. B, Photomicrographs of serial sections from the brains of Gli1$^{het}$;RCE mice on a regular or cuprizone diet (at the peak of demyelination) stained with Black-Gold myelin (left panels) or immunostained for GFP (right panels). The inset in the upper left panel shows a coronal section of the forebrain; the box highlights the area of the Corpus Callosum (CC) analyzed. The black arrow in the lower left panel indicates a demyelinated region of the CC. Labeled cells in the CC are restricted to the site of demyelination (white arrow). Scale bar, 100 µm. C, Schematic of the experimental time course for lysophosphatidyl-choline (LPC) model. D, Photomicrographs of sections through the CC of mice injected with saline (left panel) or LPC (right panel) Immunofluorescence shows numerous GFP-labeled cells in the CC at the site of LPC injection. Scale bar, 50 µm. CC=Corpus Callosum.

The present invention is based on an unexpected observation that Sonic Hedgehog (SHH) signaling inhibits remyelination. Data presented in Example 1, below, indicates that SHH-responsive adult neural stem cells, which are enriched in the subventricular zone (SVZ), are robustly recruited to demyelinated lesions of the subcortical white matter, whereas in the absence of demyelination, these cells do not enter white matter tracts. As further demonstrated herein (see Example 2, below), recruitment of these SHH-responsive cells and their differentiation into oligodendrocytes is significantly enhanced by genetic ablation or pharmacological inhibition of the Gli1 transcription factor Inhibition of Gli1 is well tolerated and does not deplete the SVZ stem cell pool. Together, these studies show that endogenous neural stem cells can be mobilized for repair of demyelinated lesions by inhibiting Gli1. Based on these observations, the present invention provides a method of enhancing remyelination by endogenous stem cells (i.e., the generation of new myelin sheaths) to repair demyelinated axons by inhibiting Gli1 transcription factor. Enhancing remyelination is a currently unmet but critical goal in treating various neurological disorders characterized by myelin loss or myelin deficiency. Remyelination of demyelinated axons is expected to be neuroprotective as well, a further unmet goal in all demyelinating disorders in the CNS and PNS. The method of the present invention provides a therapeutic strategy for treating MS as well as other neurological disorders characterized by myelin loss or myelin deficiency. This therapeutic strategy also more broadly enhances remyelination by other cells, e.g., oligodendrocyte precursors, in the brain, not just the stem cells.

DEFINITIONS

As used herein, the term "neurological disorder characterized by myelin loss or myelin deficiency" encompasses any disease associated with the destruction or removal of myelin, the fatty sheath surrounding and insulating nerve fibers, from nerves. Non-limiting examples of disorders characterized by myelin loss or myelin deficiency include, for example, multiple sclerosis (MS) (e.g., Relapsing/Remitting Multiple Sclerosis, Secondary Progressive Multiple Sclerosis, Progressive Relapsing Multiple Sclerosis, Primary Progressive Multiple Sclerosis, and Acute Fulminant Multiple Sclerosis), Central Pontine Myelinolysis, Acute Disseminated Encephalomyelitis, Progressive Multifocal Leukoencephalopathy, Subacute S clerosing Panencephalitis, Post-infectious Encephalomyelitis, Chronic Inflammatory Demyelinating Polyneuropathy, Devic's Disease, Balo's Concentric Sclerosis, the leukodystrophies (e.g., Metachromatic Leukodystrophy, Krabbe disease, Adrenoleukodystrophy, Pelizaeus-Merzbacher disease, Canavan disease, Childhood Ataxia with Central Hypomyelination, Alexander disease, or Refsum disease), optic neuritis, transverse myelitis, cerebral palsy, spinal cord injury, age-associated myelin deficiency, as well as acquired and inherited neuropathies in the peripheral nervous system (e.g., Guillain-Barre Syndrome and Charcot Marie Tooth disease).

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

In the context of the present invention insofar as it relates to any of the disease conditions recited herein, the terms "treat", "treatment", and the like mean to relieve or alleviate at least one symptom associated with such condition, or to slow or reverse the progression of such condition. Within the meaning of the present invention, the term "treat" also denotes to arrest, delay the onset (i.e., the period prior to clinical manifestation of a disease) and/or reduce the risk of developing or worsening a disease. For example, in relation to neurological disorders characterized by myelin loss or myelin deficiency, the term "treat" may mean to delay manifestation, arrest the progression, relieve or alleviate at least one symptom of a neurological disorder characterized by myelin loss or myelin deficiency such as, but not limited to, impaired vision or cognitive function, numbness, weakness in extremities, tremors or spasticity, heat intolerance, speech impairment, incontinence, dizziness, impaired proprioception (e.g., balance, sense of limb position) or coordination, pain, memory, depression, and gait disorders.

As used herein, the term "remyelination" refers to the generation of new myelin sheaths. Remyelination can be monitored by methods which include direct determination of the state of myelin in the subject, e.g., one can measure white matter mass using magnetic resonance imaging (MRI), measure the thickness of myelin fibers using a magnetic resonance spectroscopy (MRS) brain scan, or any other direct measures known in the art (e.g., Positron-Emission Tomography (PET), Diffusion-Weighted Imaging (DW-I, or DW-MRI), Diffusion Tensor Imaging, Myelography, Magnetization Transfer, etc.). Treatment effectiveness can be also monitored by detecting a reduction in the size or number of inflammatory lesions (i.e., scleroses) present in the patient; monitoring a patient's cerebrospinal fluid (e.g., obtained by a lumbar puncture) for a reduction in the presence or amount of, e.g., (i) abnormal proteins such as tiny fragments of myelin, (ii) elevated levels of or specific types of lymphocytes, and/or (iii) abnormal levels of immunoglobulin (IgG) molecules; monitoring a patient for a positive change in neuropsychology (e.g., the status of various abilities such as memory, arithmetic, attention, judgment and reasoning); and/or monitoring a patient's urine for a decrease in levels of myelin basic protein-like material (MBPLM). Certain tests for color blindness can also be helpful in tracking the treatment of demyelinating disorders on the eyes. Whitaker et al. (1995) Ann Neurol. 38(4):635-632.

In some embodiments, at least a 5% (e.g., at least 10%, at least 15%, at least 20%, at least 25%, at least 30%, at least 35%, at least 40%, at least 50%, at least 60%, at least 70%) improvement in one or more symptoms of a neurological disorder characterized by myelin loss or myelin deficiency or other above-described indicia following a remyelination therapy of the invention is sufficient to classify the patient as responding to a therapy.

As used herein the term "therapeutically effective" applied to dose or amount refers to that quantity of a compound or pharmaceutical composition that is sufficient to result in a desired activity upon administration to a subject in need thereof. Within the context of the present invention, the term "therapeutically effective" refers to that quantity of a compound (e.g., Gli1 inhibitor) or pharmaceutical composition containing such compound that is sufficient to delay the manifestation, arrest the progression, relieve or alleviate at least one symptom of a neurological disorder characterized by myelin loss or myelin deficiency. Note that when a combination of active ingredients is administered the effective amount of the combination may or may not include amounts of each ingredient that would have been effective if administered individually.

The phrase "pharmaceutically acceptable", as used in connection with compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

As used herein, the term "subject" refers to any mammal. In a preferred embodiment, the subject is human.

In accordance with the present invention, there may be employed conventional molecular biology, microbiology, and recombinant DNA techniques within the skill of the art. See, e.g., Sambrook, Fritsch and Maniatis, Molecular Cloning: A Laboratory Manual, 2nd ed., Cold Spring Harbor Laboratory Press, Cold Spring Harbor, N.Y., 1989 (herein "Sambrook et al., 1989"); DNA Cloning: A Practical Approach, Volumes I and II (Glover ed. 1985); Oligonucleotide Synthesis (Gait ed. 1984); Nucleic Acid Hybridization (Hames and Higgins eds. 1985); Transcription And Translation (Hames and Higgins eds. 1984); Animal Cell Culture (Freshney ed. 1986); Immobilized Cells And Enzymes (IRL Press, 1986); B. Perbal, A Practical Guide To Molecular Cloning (1984); Ausubel et al. eds., Current Protocols in Molecular Biology, John Wiley and Sons, Inc. 1994; among others.

Gli1 Inhibitors Useful in the Methods of the Invention

Gli1 inhibitors that can be used in the methods of the invention include, but are not limited to, small molecule Gli1 antagonists such as, e.g., GANT61 (Gli-ANTagonist 61) and GANT58 (NSC 136476 and NSC 75503, respectively) disclosed in Lauth, M. et al., Proc. Natl. Acad. Sci. USA, 2007, 107, 8455-8460 as well as related symmetric and non-symmetric N,N-bisbenzylated hexahydropyrimidines and tetrahydroimidazoles described in International Publication No. WO2007/139492. Mechanistically, both GANT61 and GANT58 inhibitors act at the nucleus to block Gli function, and GANT61 interferes with DNA binding of Gli1. Both compounds display selectivity for the Hh pathway over several unrelated signal-transduction pathways such as TNF/NFkN signaling, glucocorticoid receptor gene transactivation, and the Ras-Raf-Mek-Mapk cascade (Peukert and Miller-Moslin, ChemMedChem, 2010, 5, 500-512).

Other Gli1 inhibitors that can be used in the methods of the invention include, but are not limited to, phytoestrogens genistein and epigallocatechin gallate (EGCG) (International Publication No. WO2008/131354); sesquiterpenes zerumbone and zerumbone epoxide; bisindole alkaloids staurosporinone, 6-hydroxystaurosporinone, arcyriaflavin C, and 5,6-dihydroxyarcyriaflavin A; and physalins F and B. (Hosoya, T. et al. (2008) ChemBioChem 9:1082); peptides consisting of fragments from SuFu (International Publication No. WO2001/012655).

Other Gli1 inhibitors useful in the methods of the invention are Gli1-mediated transcription inhibitors containing a tyramine amide moiety disclosed in Mahindroo et al., J. Med. Chem. 2009, 52, 4277-4287, in particular, NMDA298-1 and JK184. See also Lee et al., ChemBioChem 2007, 8, 1916-1919. Additional useful small molecule inhibitors of Gli1 are HPI-1 through HPI-4 disclosed in Hyman et al., Proc. Natl. Acad. Sci. USA 2009, 106, 14132-14137.

For review on various inhibitors of Gli1 see Peukert and Miller-Moslin, ChemMedChem, 2010, 5, 500-512). Additional small molecule inhibitors can be identified, e.g., using the Gli-luciferase reporter gene assay disclosed in Lauth, M. et al., Proc. Natl. Acad. Sci. USA, 2007, 107, 8455-8460 or the cell-based reporter assay of Gli1-mediated transcription disclosed in Hosoya, T. et al. (2008) ChemBioChem 9:1082.

siRNAs inhibiting Gli1 expression are also useful as inhibitors of the present invention. For example, U.S. Pat. No. 7,666,676 discloses Gli1 siRNAs GUCAUUAUCAAAUUU-CUCCTT (SEQ ID NO: 2); AGAAGAAAAGAGUGGGC-CCTT (SEQ ID NO: 3); UCCGGUGUUUUCUUCAUCCTT (SEQ ID NO: 4); GAGAUCUUCCCUUCAUACCTT (SEQ ID NO: 5). Sanchez et al., Proc Natl Acad Sci USA 2004, 101:12561-6 discloses Gli1 siRNA AACUCCACAG-GCAUACAGGAU (SEQ ID NO: 6). For additional RNAi sequences see, e.g., U.S. Pat. No. 7,709,454 and Stecca et al., Proc. Natl. Acad. Sci. USA 2007; 104:5895-900.

In one aspect, this disclosure features a method for treating multiple sclerosis. The method includes administering to a subject in need thereof an effective amount of a Gli1 inhibitor. In some embodiments, the Gli1 inhibitor can be any of the compounds of formula (1):

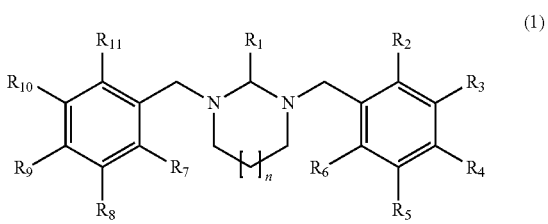

in which n is 0, 1, or 2; $R_1$ is $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; and each of $R_2$, $R_3$, $R_4$, $R_5$, $R_6$, $R_7$, $R_8$, $R_9$, $R_{10}$, and $R_{11}$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, $OR_a$, $COOR_a$, $OC(O)R_a$, $C(O)R_a$, $C(O)NR_aR_b$, or $NR_aR_b$, in which each of $R_a$ and $R_b$, independently, is H, $C_1$-$C_{10}$ alkyl, $C_3$-$C_{20}$ cycloalkyl, $C_1$-$C_{20}$ heterocycloalkyl, aryl, or heteroaryl.

A subset of the compounds of formula (1) are those in which n is 1. In these compounds, $R_1$ can be heteroaryl (e.g., 4-pyridyl); each of $R_2$ and $R_{11}$ can be $NR_aR_b$ (e.g., $N(CH_3)_2$), and each of $R_3$, $R_4$, $R_5$, $R_6$, $R_7$, $R_8$, $R_9$, and $R_{10}$ can be H. An exemplary compound of formula (1) is

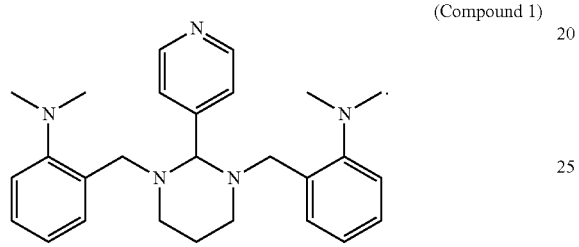

(Compound 1)

The term "alkyl" refers to a saturated, linear or branched hydrocarbon moiety, such as —$CH_3$ or —$CH(CH_3)_2$. The term "alkenyl" refers to a linear or branched hydrocarbon moiety that contains at least one double bond, such as —CH=CH—$CH_3$. The term "alkynyl" refers to a linear or branched hydrocarbon moiety that contains at least one triple bond, such as —C≡C—$CH_3$. The term "cycloalkyl" refers to a saturated, cyclic hydrocarbon moiety, such as cyclohexyl. The term "cycloalkenyl" refers to a non-aromatic, cyclic hydrocarbon moiety that contains at least one double bond, such as cyclohexenyl. The term "heterocycloalkyl" refers to a saturated, cyclic moiety having at least one ring heteroatom (e.g., N, O, or S), such as 4-tetrahydropyranyl. The term "heterocycloalkenyl" refers to a non-aromatic, cyclic moiety having at least one ring heteroatom (e.g., N, O, or S) and at least one ring double bond, such as pyranyl. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl. Cycloalkyl, cycloalkenyl, heterocycloalkyl, heterocycloalkenyl, aryl, and heteroaryl mentioned herein can include one cyclic ring or more than one (e.g., two or three) cyclic rings. In addition, cycloalkyl, cycloalkenyl, heterocycloalkyl, heterocycloalkenyl, aryl, and heteroaryl can also include moieties in which two or more of the just-mentioned groups are fused with each other.

Alkyl, alkenyl, alkynyl, cycloalkyl, cycloalkenyl, heterocycloalkyl, heterocycloalkenyl, aryl, and heteroaryl mentioned herein include both substituted and unsubstituted moieties, unless specified otherwise. Possible substituents on cycloalkyl, cycloalkenyl, heterocycloalkyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, nitroso, azido, acyl, thioacyl, acyloxy, carboxyl, and carboxylic ester. On the other hand, possible substituents on alkyl, alkenyl, or alkynyl include all of the above-recited substituents except $C_1$-$C_{10}$ alkyl.

In some embodiments, the Gli1 inhibitor can be

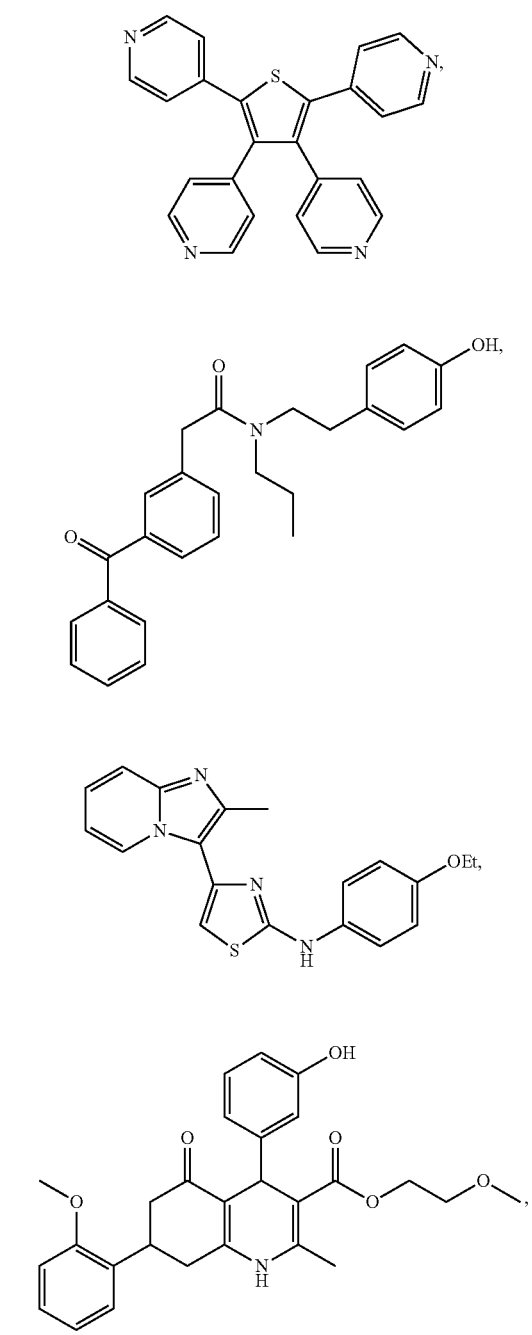

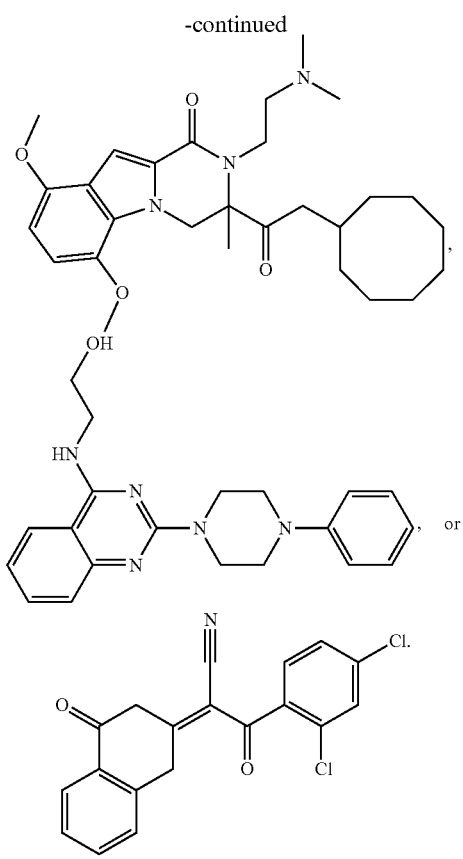

Other exemplary Gli1 inhibitors are described in, for example, WO 2007/139492, U.S. Application Publication No. 2011/0183962, U.S. Pat. No. 7,666,676, Hosoya et al., ChemBioChem, 2008, 9, 1082-1092, Tremblay et al., Expert Opin. Ther. Patents, 2009, 19(8):1039-1056, and Peukert et al., ChemMedChem, 2010, 5, 500-512, the entire contents of which are hereby incorporated by reference.

Compositions and Administration

The Gli1 inhibitor-containing compositions of the invention can be simple aqueous (e.g., saline) solutions. Alternatively, they can contain various additional ingredients which enhance stability and/or delivery of the Gli1 inhibitor. Such additional ingredients are well known in the art.

In addition to a Gli1 inhibitor, the composition of the invention may further comprise one or more additional therapeutic ingredients (or active substances). These therapeutic ingredients can be any compound that elicits a desired activity or therapeutic or biological response in the subject. Non-limiting examples of useful additional therapeutic ingredients is provided in the Combination Treatments section, below.

The compositions of the invention may further comprise agents which facilitate brain delivery. Non-limiting examples of such useful agents include, e.g., an implantable reservoir (Omaya reservoir), functionalized nanocarriers (e.g., nanoparticles coated with transferrin or transferrin receptor [TR] antibodies) and liposomes (e.g., liposomes coated with targeting molecules such as antibodies, Trojan Horses Liposomes [THL]), antibodies (e.g., antibodies against transferrin receptor [TR] and insulin receptor [HIR], BBB transmigrating Llama single domain antibodies (sdAb)), chimeric peptides (e.g., Angiopeps derived from proteins expressing the Kunitz domain), low-density lipoprotein receptor related proteins 1 and 2 (LRP-1 and 2), diphtheria toxin receptor (DTR), mesenchyme stem cells, etc.

The optimal therapeutic concentration of the Gli1 inhibitor in the pharmaceutical compositions of the present invention will necessarily depend upon the activity of the specific Gli1 inhibitor being used, characteristics of the patient and the nature of the neurological disease for which the agent is being used. In addition, the concentration of the Gli1 inhibitor will depend upon the stage of a particular disease or disorder and the extent of myelin loss, e.g., early vs. late MS.

Dosage regimens should be adjusted to provide an optimum activity for a specific disease and patient. Dosages should also be adjusted based on the release rate of the administered formulation.

The amount of active compound will generally be chosen to provide effective treatment upon as few administrations as possible (this is particularly important for achieving compliance in a patient population with memory defects). Preferably, the administration should be once daily.

Combination Treatments of the Invention

In the treatment methods of the invention, Gli1 inhibitors can be administered in combination with various other treatments which can be useful for neurological disorders characterized by myelin loss or myelin deficiency. For example, Gli1 inhibitors can be administered in combination with at least one of Interferon Beta 1a (Avonex), Interferon Beta 1b (Rebif), glatiramer acetate (Copaxone), mitoxantrone (Novantrone), azathiprine (Imuran), cyclophosphamide (Cytoxan or Neosar), cyclosporine (Sandimmune), ampyra, dimethyl fumarate (BG12), fingolimod, methotrexate, Cladribine (Leustatin), methylprednisone (Depo-Medrol or Solu-Medrol), prednisone (Deltasone), prednisolone (Delta-Cortef), dexamethasone (Medrol or Decadron), adreno-corticotrophic hormone (ACTH), Corticotropin (Acthar), anti-integrin specific antibodies, cytoxan, naltrexone, and the like. Gli1 inhibitors can be also administered in combination with anti-LINGO therapies, axin/Wnt pathway inhibitors, and/or agonists for RXR transcription factors such as, e.g., 9-cis-retinoic acid (Fancy et al., 2011; Huang et al., 2011a; Huang et al., 2011b; Mullard, 2011).

Following the disclosure of Example 4, below, Gli1 inhibitors can be also administered in combination with an agent which causes upregulation and/or increases activity of Gli2 and/or Gli3. Non-limiting examples of such agents include, for example, Shh agonists and Protein Kinase A inhibitors (PKA inhibitors). Specific examples of useful Shh agonists and PKA inhibitors are provided, for example, in U.S. Pat. Nos. 6,767,888 and 6,683,192. See also examples of various PKA inhibitors in the 2012 Enzo Life Sciences product catalog.

In addition, Gli1 inhibitors can be administered in combination with an agonist of smoothened (Smo). Examples of useful Smo agonists are disclosed, for example, in Int. Pat. Appl. Publ. No. WO2003027234; Chen et al., Proc. Natl. Acad. Sci. U.S.A., 99(2):14071-14076, 2002 (e.g., N-Methyl-N'-(3-Pyridinylbenzyl)-N'-(3-Chlorobenzo[b]thiophene-2-carbonyl)-1,4-Diaminocyclohexane (SAG)); Frank-Kamenetsky et al., J. Biol., I:10, 2002.

EXAMPLES

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Materials and Methods

Mice.

Gli1-LacZ mice (Bai et al., 2002, Development 129(20): 4753-61; commercially available from Jackson laboratories); Gli1-CreER mice (Ahn and Joyner, 2004, Cell 118(4):505-16; commercially available from Jackson laboratories); Rgfp mice (Sousa et al., 2009, Cereb Cortex, Suppl 1:i1-10); Nestin-CreER mice (Balordi and Fishell, 2007, J Neurosci, 27(52):14248-59); Smo-floxed mice (Long et al., 2001, Development, 128(24):5099-5108; commercially available from Jackson laboratories). Gli1-null mice which lack the expression of Gli1 were generated using Gli1-CreER and Gli1-LacZ mice and Rgfp mice.

Also, mice were generated which are either heterozygous or null for Gli1 and have constitutively active Smo due to a point mutation W539L in the gene (SmoM2 mice from Jackson Laboratories) that can be conditionally activated by cre-lox recombination. Specifically, the Gli1$^{CreER/+}$ mice and Gli1$^{CreER/LacZ}$ mice were mated to SmoM2$^{c/c}$ mice and Gli1$^{CreER/+}$;SmoM2$^{c/c}$ (Gli1-het; SmoM2) and Gli1$^{CreER/LacZ}$;SmoM2$^{c/c}$ (Gli1-null; SmoM2) mice were obtained.

Fate Mapping and Demyelination.

10 week old mice were administered 5 mg Tamoxifen (Sigma) in corn oil on alternate days for total of 4 intraperitoneal (i.p.) injections. Gli1$^{het}$;RCE, mice, maintained on the Swiss-Webster background, were fed 0.4% cuprizone (Matsushima and Morell, 2001, Brain Pathol., 11:107-116; Elsworth & Howell, Research in Veterinary Science, 14:385-387, 1973). Gli1$^{het}$;Smo$^{M2}$ mice were maintained on the C57Bl/6 background and fed 0.2% cuprizone to obtain comparable demyelination in the corpus callosum (CC) (Elsworth & Howell, Research in Veterinary Science, 14:385-387, 1973). For the LPC model, 2 μl 1% LPC (Calbiochem) were stereotaxically injected into the CC at 1.5 mm anterior, 1.2 mm lateral and 2.2 mm ventral to bregma.

Drug Infusion.

GANT61 (Enzo Life Sciences product #ALX-270-482) (5.6 mg/Kg per day; compound in 50% DMSO and 15% Ethanol in PEG400) or vehicle (50% DMSO+15% Ethanol in PEG400) were delivered via mini-osmotic pump (model 2004, Durect) at a rate of 0.25 μl/h for 4 weeks into the lateral ventricle of Gli$^{het}$;RCE mice at 0.5 mm Anterior, 0.75 mm lateral and 2.5 mm ventral to the bregma.

Immunostaining and Analysis.

For Black-Gold (Millipore) staining, mice were perfused with 4% PFA and 20 μm coronal sections were stained according to manufacturer's protocol. For all other analysis, mice were perfused with Prefer (Anatech) and 20 μm coronal sections were stained with X-gal (Ahn & Joyner, Nature, 437:894-897, 2005) or processed for immunofluorescence with rabbit anti-GFP (1:1,000, Invitrogen) and one of the following antibodies: rat anti-PDGFRα (1:200, BD Biosciences); rabbit anti-NG2 (1:200, Millipore) and β4 spectrin (1:4,000 from M. Rasband); mouse anti-CC1 (1:400, Calbiochem), anti-GFAP (1:400, Sigma), anti-MOG (1:50, Sigma) and guinea pig anti-Caspr (1:3,000 from M. Bhat). Secondary antibodies were goat anti-species conjugated to Alexafluor-488, 594 or -680 (1:1,000, Molecular Probes). Nuclei were counterstained with Hoechst 33258 (1:5,000, Invitrogen). Fluorescent images were obtained as Z-stacks of 1 μm optical sections using a confocal laser-scanning microscope (LSM 510, Zeiss) and processed using Adobe Photoshop. At least 10 sections/mouse were analyzed and data from at least 3 mice were combined to determine the average and standard deviation. Student's t-test was performed to calculate P values.

Example 1

SHH Signaling Pathway is a Useful Therapeutic Target for Remyelination

The failure of oligodendrocytes (OL) to remyelinate effectively in multiple sclerosis (MS) leads to progressive deterioration of neurological function due to conduction block and neuronal degeneration. A key therapeutic goal is to identify the mechanisms that limit remyelination in order to develop new strategies to enhance remyelination and repair in MS. Recent evidence suggests that progenitor cells in the subventricular zone (SVZ) give rise to OLs (Menn et al., 2006; Picard-Riera et al., 2002).

Sonic Hedgehog (Shh) is a secreted morphogen required for the generation of OLs during development and for maintenance of stem cells in the adult SVZ. Binding of Shh to its receptor relieves the transmembrane protein smoothened (smo) from inhibition and results in transcription of Gli proteins, which are downstream effectors of Shh signaling.

The contribution of Shh-responsive cells and of Shh signaling during remyelination was examined Gli1-CreER$^{T2}$; RCE mice were utilized in which tamoxifen treatment results in permanent expression of cytoplasmic green fluorescent protein (GFP) in all Gli1-expressing, i.e. Shh-responsive cells and their progeny (Ahn & Joyner, Cell, 118:505-516, 2004; Sousa et al., Cerebral cortex, 19 Suppl 1, i1-10, doi:10.1093/cercor/bhp038, 2009). The fate of the Shh-responsive cells was then followed after inducing demyelination in the mouse Corpus Callosum (CC) by either: i) dietary cuprizone, which results in patchy myelin loss (Matsushima & Morell, Brain Pathol., 11:107-116, 2001) or ii) by direct, stereotactic injection of the detergent lysophosphatidyl-choline (LPC) into the callosum (Gensert & Goldman, Neuron, 19: 197-203, 1997).

Figure 1B:
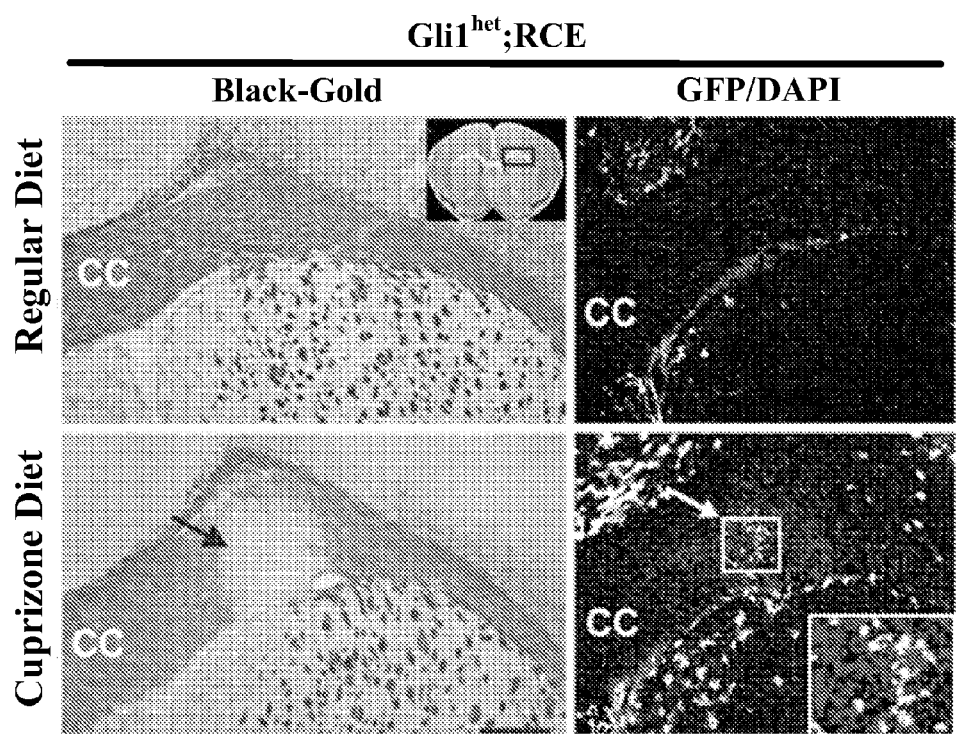
Figure 1C:
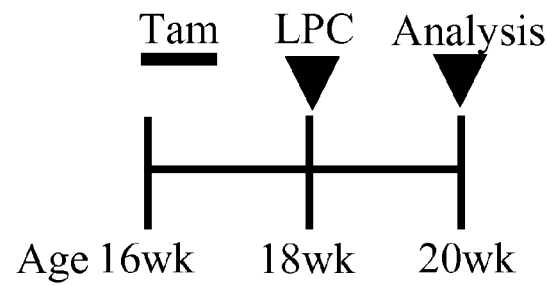
Figure 1D:
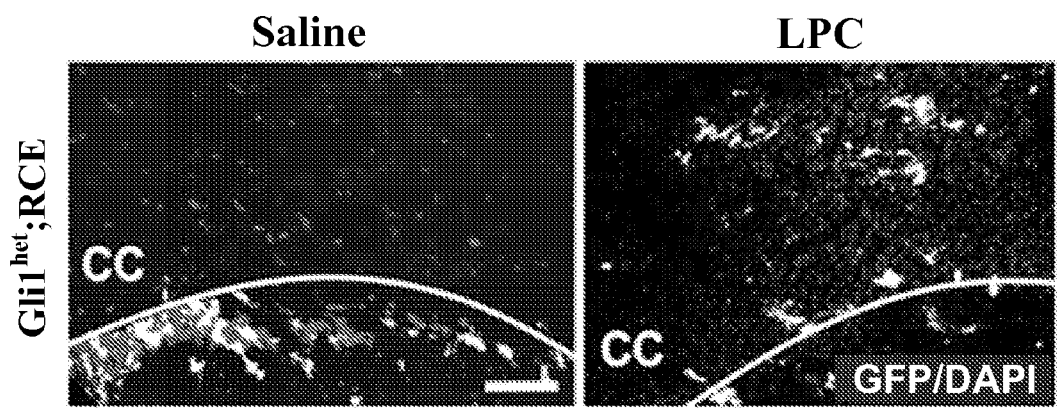

Demyelination of tamoxifen treated, adult Gli1$^{CreER/wt}$; RCE (Gli1$^{het}$;RCE) mice (n=3) was first induced with 6 weeks of dietary cuprizone, which corresponds to the period of peak demyelination in this paradigm (FIGS. 1a, b). Analysis of serial sections of the brains showed that GFP-expressing cells (17.3±2.6 per section) are recruited to areas of demyelination in the treated mice, whereas no labeled cells were observed in the CC of controls (FIG. 1b). Similar results were observed when demyelination was induced by LPC injection into tamoxifen treated Gli1$^{het}$;RCE mice (n=3) and the brains were analyzed 2 weeks later (FIG. 1c). Thus, GFP-labeled cells were evident at the site of LPC-induced demyelination but not of saline injected brains (FIG. 1d). These results indicate that Gli1-expressing cells are recruited specifically to areas of demyelination and do not enter the healthy CC or other white matter tracts in the brain (FIG. 1b,d). Thus, the present inventors have identified and fate mapped a population of stem cells in the adult SVZ, which enter the white matter in specific response to demyelination.

Figure 2A:
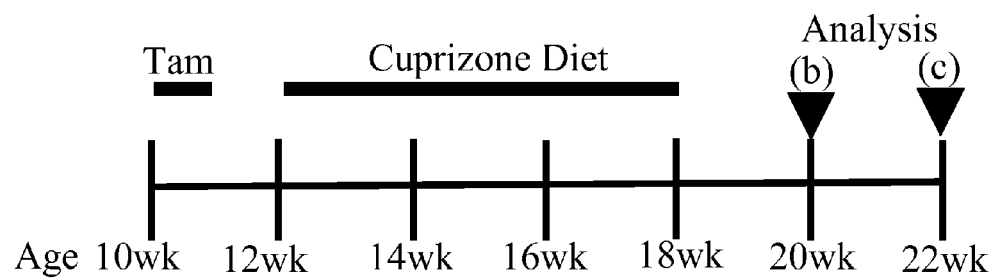
FIGS. 2A-C demonstrate that Shh-responsive cells generate myelinating oligodendrocytes following demyelination. A, Schematic of the experimental time course. B, 2 weeks after removal from the cuprizone diet, GFP-labeled cells in the Corpus Callosum (CC) of Gli1$^{het}$;RCE mice co-expressed the oligodendroglial progenitor markers PDGFRα and NG2, the mature oligodendrocyte marker CC1, and the astrocytic marker GFAP (arrows). Scale bar, 10 µm. C, 4 weeks after removal from the cuprizone diet, GFP-labeled cells had acquired the morphology of myelinating oligodendrocytes (upper left panel). GFP-labeled processes of cells colocalized with the myelin protein MOG and were associated with the nodal marker β4 spectrin, present between two GFP+ internodes, and the paranodal marker Caspr. Scale bar, 10 µm.
Figure 2B:
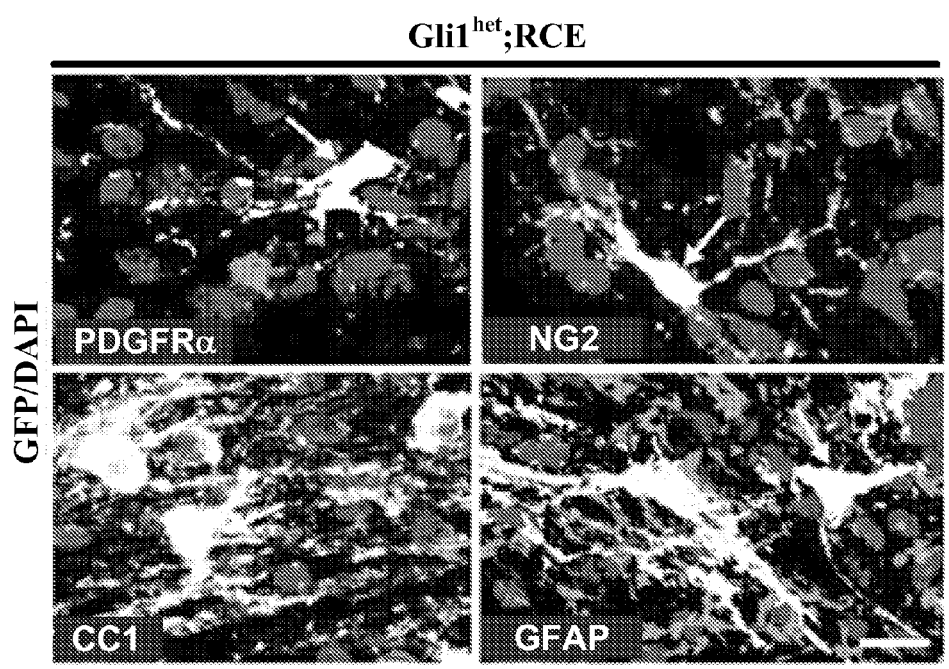
Figure 2C:
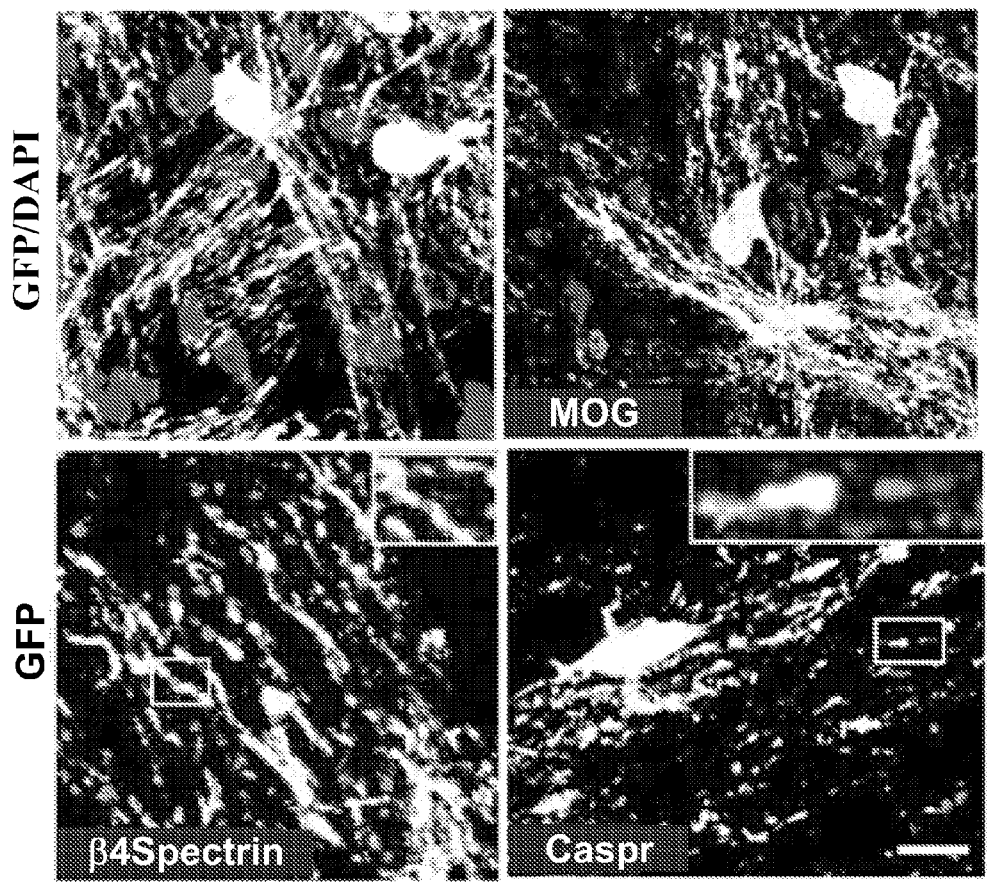

The present inventors next investigated the fate of the GFP-labeled cells in the CC during the period of remyelination that ensues after cuprizone is removed from the diet (FIG. 2a). At two weeks of recovery, labeled cells in the CC differentiated exclusively into glia, generating both GFAP-expressing astrocytes (15.5±4.1%) and oligodendroglia including OPCs (9.8±8.7%) and CC1+-oligodendrocytes (40.2±15.1%; n=3, FIG. 2b). None of the GFP-labeled cells co-expressed neuronal (NeuN) or microglial (Iba1 and CD11b) markers. To investigate whether the newly generated oligodendrocytes myelinated axons, the expression of myelin proteins and formation of nodal markers were studied. Four weeks after removing dietary cuprizone, many GFP-labeled cells had acquired a morphology consistent with that of myelinating oligodendrocytes (FIG. 2c). Further, GFP-labeled processes frequently expressed the myelin protein MOG and were associated with the formation of paranodes, demarcated by the axonal paranodal protein Caspr, and of nodes of Ranvier, identified by β4 Spectrin expression (n=3, FIG. 2c). Taken together, these data indicate that Gli1-expressing stem cells in the SVZ are recruited to areas of demyelination where they differentiate into mature, myelinating oligodendrocytes.

Figure 5:
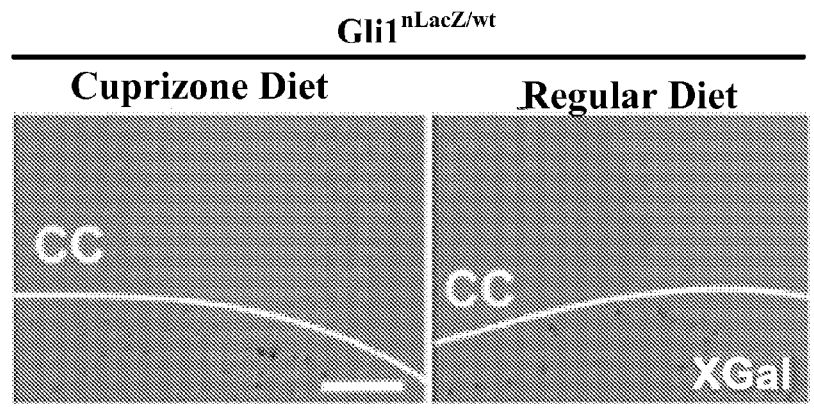
FIG. 5. Brains of Gli1$^{nLacZ}$ mice were analyzed by X-gal staining 2 weeks after removal from the cuprizone diet. No X-gal-positive cells were seen in the Corpus Callosum (CC) of mice on either a regular or a cuprizone diet. Scale bar, 50 µm. CC=Corpus Callosum.

To examine whether cells that enter sites of demyelination in the CC were actively responding to Shh, $Gli1^{nLacZ}$ mice which express nuclear LacZ from the Gli1 locus (Bai et al., Development, 129:4753-4761, 2002) were analyzed. No LacZ labeled cells were detected in the CC either before or after demyelination (n=3, FIG. 5) indicating that the glial cells generated from Gli1-expressing stem cells are not responding to Shh once they enter the callosum. Since cells in the normal adult CC also do not express LacZ, these results show that the resident progenitors in the white matter do not actively signal via Shh.

To further distinguish between a source of cells migrating out from subventricular zone (SVZ) from those resident within the CC, time-course experiments were performed in both $Gli1^{het}$;RCE and $Gli1^{nlacZ}$ mice. Demyelination in the $Gli1^{het}$;RCE mice was produced by LPC injection following tamoxifen administration and then the brains were analyzed on days 1 to 6 (n=3 each). Demyelination was evident within a day after LPC injection. However, the first GFP-labeled cells were not observed in the CC until 3 days post-LPC injection and their numbers continued to increase at later time points. In a similar experiment with $Gli1^{nlacZ}$ mice, no LacZ-labeled cells were detected in the CC at any time (n=3 each). Furthermore, when tamoxifen was administered to $Gli1^{het}$; RCE mice 2 days after LPC demyelination, no GFP-labeled cells were observed in the CC (n=3). These studies suggest that the labeled cells require several days to migrate from the SVZ to the CC following demyelination.

Figure 3A:
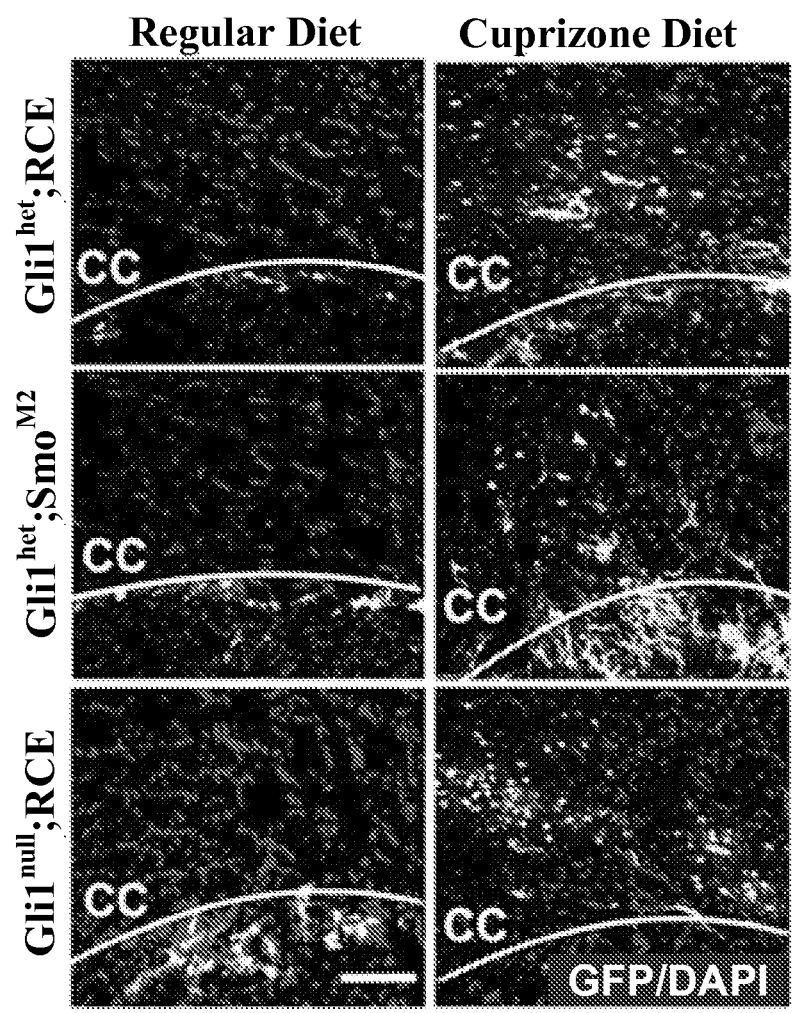

Since Shh signaling is important for the specification of the oligodendroglial lineage and proliferation of OPCs, the present inventors hypothesized that enhancing the activity of this pathway would be beneficial during remyelination by recruiting more stem cells for repair. To activate this pathway specifically in Gli1-expressing stem cells, $Gli1^{CreER}$; $RsmoM2^{fx/fx}$ ($Gli1^{het}$;$Smo^{M2}$) mice were generated in which the activated SmoM2 allele (fused to a GFP tag) is expressed after tamoxifen treatment (Jeong et al., Genes & Development, 18:937-951, 2004). Tamoxifen was administered to these mice prior to feeding them either a regular or a cuprizone diet for 6 weeks. When these mice were examined 2 weeks after recovery from the cuprizone diet, labeled cells were observed in the CC only in mice that had undergone demyelination (FIG. 3a). The number of labeled cells in the CC of the $Gli1^{het}$;$Smo^{M2}$ mice (5.6±2.9 per section, n=3) was modestly reduced compared to the $Gli1^{het}$;RCE mice following demyelination (FIG. 3b). $Gli1^{het}$;$Smo^{M2}$ mice also had a greater proportion of labeled oligodendrocyte progenitors (57.5±23.2%) than the $Gli1^{het}$;RCE mice (9.8±8.7%), although neither difference was statistically significant (FIG. 3c). These results indicated that increasing the activity of Shh pathway does not enhance the recruitment of stem cells for remyelination. Thus these findings were contrary to the expectations resulting from prior publications.

Example 2

Gli1 Inhibition Results in Enhanced Remyelination by Stem Cells

Figure 6A:
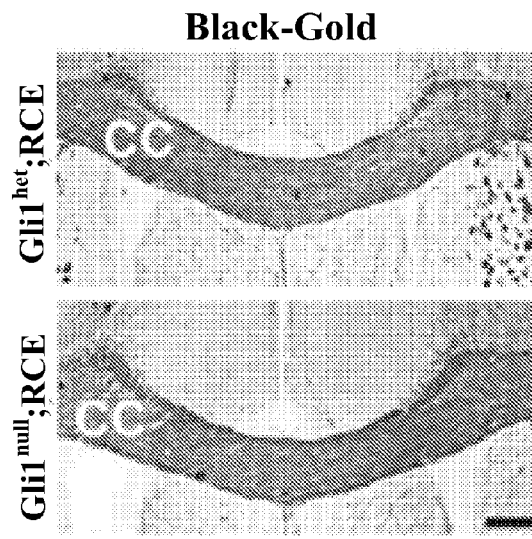
FIGS. 6A-B. A, Black-Gold myelin staining of the Corpus Callosum (CC) of adult Gli1$^{het}$;RCE and Gli$^{null}$;RCE mice shows no difference in the extent of myelination. Scale bar, 100 µm. B, Gli1$^{het}$;RCE and Gli1$^{null}$;RCE mice received tamoxifen injections 6 weeks prior to starting either a regular or a cuprizone diet; brains were analyzed 2 weeks after cessation of cuprizone. The numbers of neural stem cells in the subventricular zone (SVZ) were quantified as the percentage of GFP-labeled cells co-expressing GFAP. The percentage of GFAP+GFP cells in the SVZ of mice receiving cuprizone diet was comparable to those on a regular diet. n=3. Data are mean±standard deviation. Student's T test. CC=Corpus Callosum.

Since Gli1 expression is induced by the highest levels of Shh, the present inventors investigated the role of Gli1 in the recruitment and differentiation of these Shh-responsive cells during remyelination. To this end, $Gli1^{CreER/nLacZ}$;RCE ($Gli1^{null}$;RCE) mice were generated to genetically map the fate of cells lacking Gli1. Brains from healthy adult mice were first examined by staining with Black-Gold myelin stain; no defects in myelination were evident compared to $Gli1^{het}$;RCE mice (FIG. 6a). These results are consistent with previous studies reporting normal CNS development in the $Gli1^{null}$ mice (Bai et al., Development, 129:4753-4761, 2002). Tamoxifen was then administered to the $Gli1^{null}$;RCE mice and they were fed either a normal diet or a diet supplemented with cuprizone. Brains from these mice were examined 2 weeks after cessation of cuprizone. In the $Gli1^{null}$;RCE mice on a normal diet, as in the $Gli1^{het}$;RCE mice, no GFP-labeled cells were seen in the CC (FIG. 3a). However, in mice undergoing remyelination, GFP-labeled cells were readily apparent, with significantly higher numbers in the CC of $Gli1^{null}$; RCE mice (63±6.5 per section, n=3) compared to $Gli1^{het}$; RCE mice (17.3±2.6 per section; FIG. 3d). In addition, a significantly higher percentage of the GFP-labeled cells were mature oligodendrocytes in the nulls compared to heterozygotes (81.3±4.4% vs. 40.2±15.1%, n=3; FIG. 3e). In toto, there were ~7.5 fold more GFP-labeled, mature oligodendrocytes in the $Gli1^{null}$ vs. the $Gli1^{het}$ mice. In contrast, the numbers of labeled oligodendrocyte progenitors in the $Gli1^{null}$;RCE vs. the $Gli1^{het}$;RCE mice were similar (5.22±2.5% vs. 9.8±8.7% n=3, FIG. 3e) and the numbers of GFAP-expressing astrocytes were significantly reduced (2.6±1.3% vs. 15.5±4.1%, n=3, FIG. 3e).

Figure 6B:
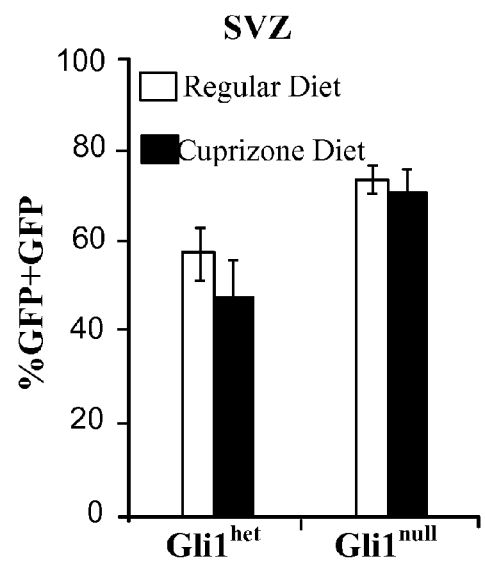

Taken together, these results indicate that Gli1 loss of function increases the recruitment of Shh-responsive stem cells to sites of demyelination and promotes their differentiation into mature oligodendrocytes. This enhanced recruitment of Gli1-null stem cells does not result in their depletion from the SVZ as the numbers of cells co-expressing GFAP and GFP in the SVZ was similar or slightly increased in $Gli1^{null}$;RCE mice compared to $Gli1^{het}$;RCE mice (FIG. 6b). Thus, the SVZ does not undergo stem cell depletion following demyelination in the absence of Gli1.

Figure 4A:
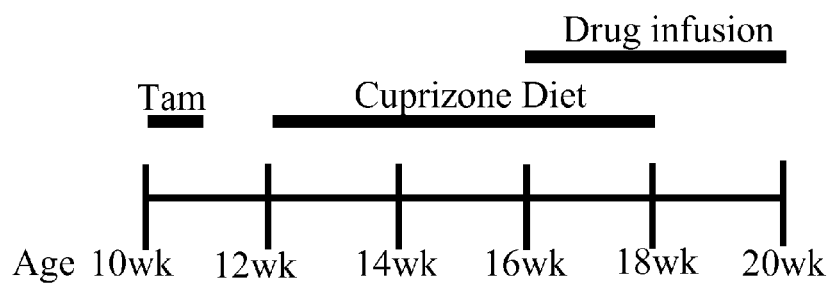
FIGS. 4A-D demonstrate that pharmacological inhibition of Gli1 increases the recruitment and differentiation of Shh-responsive cells following demyelination. A, Schematic of the experimental time-course is shown. B, Immunofluorescence for GFP shows that mice that received GANT61 had higher numbers of cells in the Corpus Callosum (CC) than mice that received saline infusion. Scale bar, 50 µm. C, Mice that had received GANT61 had ~7 fold increase in GFP-labeled cells in the CC. D, Mice receiving GANT61 infusion also had a significant increase in the percentage of mature oligodendrocytes. n=3. Data are mean±standard deviation. Student's T test: * p=0.04; ** p=0.02. CC=Corpus Callosum.
Figure 4B:
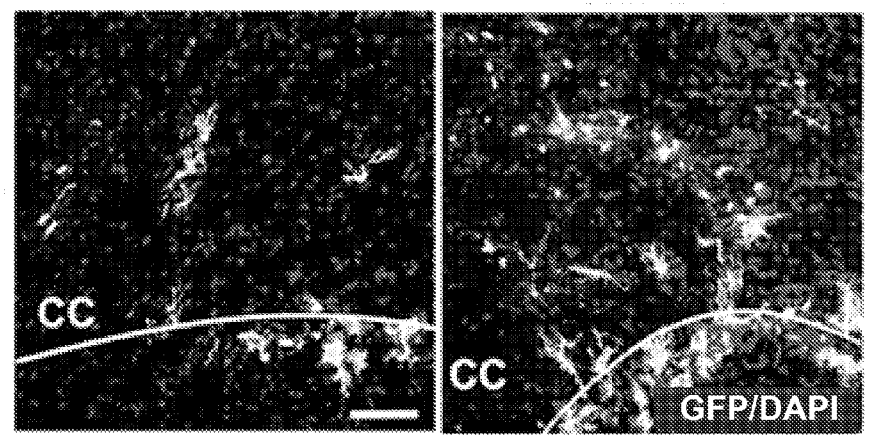
Figure 4C:
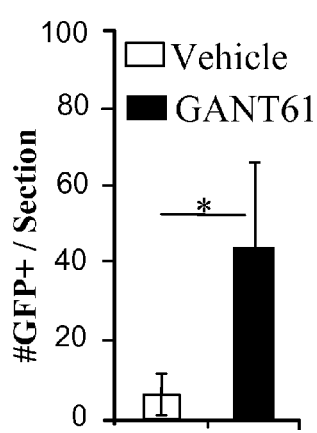
Figure 4D:
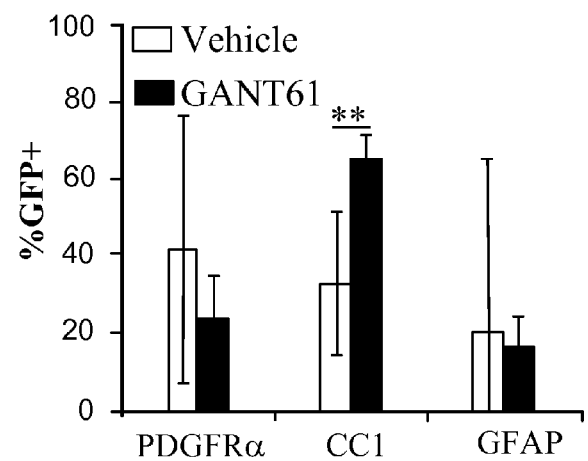

To assess whether a strategy of inhibiting Gli1 could potentially be used therapeutically, GANT61, a small molecule inhibitor of Gli1 (Lauth et al., Proc. Natl. Acad. Sci. U.S.A., 104:8455-8460, 2007), was infused into the lateral ventricle of $Gli1^{het}$;RCE mice via a mini-osmotic pump. The infusion was started after 4 weeks of cuprizone diet and was continued for an additional 2 weeks on cuprizone and 2 weeks off cuprizone for a total of 4 weeks. Mice were then sacrificed and analyzed (FIG. 4a). Mice receiving the GANT61 infusion showed significantly higher numbers of labeled cells (43.8±22.1 per section, n=3, FIGS. 4b, c) in the CC compared to those receiving vehicle infusion (6.4±5 per section, n=3). GANT61 also resulted in a significantly greater proportion of differentiated oligodendrocytes (65.4±7.5%, n=3, FIG. 4d)

compared to those receiving vehicle infusion (21.4±18.7%, n=3). These results demonstrate that Gli1 inhibitor effectively enhances the recruitment and differentiation of Shh-responsive stem cells into oligodendrocytes at sites of demyelination.

Much of the disability in the chronic stages of MS is thought to be due to progressive neurodegeneration. This degeneration occurs despite an overall reduction in inflammation and may result from the failure of remyelination in late stages of this disease (Nave & Trapp, Annu. Rev. Neurosci., 31:535-561, 2008). Thus an important, remaining therapeutic goal in MS is to enhance remyelination. The studies provided herein demonstrate that inhibiting Gli1 appears to be a well-tolerated and effective strategy for mobilizing and enhancing the differentiation of the resident population of Shh-responsive stems cells and progenitors. This approach may therefore be useful in aiding repair in MS and other demyelinating neurological disorders.

Interestingly, there were no obvious effects on normal myelin development in Gli1-deficient mice strongly suggesting that Gli1 is a dispensible transcription factor during development and in the adult. Consequently, inhibiting Gli1 may have limited or no, off-target effects.

Example 3

Studies of the Effect of Gli1 Inhibitors in Animal Models of MS

The ability of Gli1 inhibitors of the invention to treat MS will be further assessed in animal models of MS.

Experimental autoimmune encephalomyelitis (EAE) is the most commonly used model for MS. It is induced by immunization of mice and rats, primarily, with myelin antigens including myelin oligodendrocyte glycoprotein (MOG), myelin basic protein (MBP), and proteolipid protein (PLP) (Hemmer et al., Nature Reviews Neuroscience, vol. 3, no. 4, pp. 291-301, 2002). The immunization is either active (administration of the specific antigens) or passive (administration of myelin-specific T cells). Several MS features are recapitulated by EAE, including paralysis, weight loss, demyelination, and inflammation in the CNS. In the EAE model, activated myelin-specific T cells, mainly Th1 and Th17 cells, contribute to the compromise of the BBB and migrate into the CNS. In the CNS, infiltrating and local antigen presenting cells (APCs) present antigens to reactive T cells, leading to further inflammation, demyelination, and axon damage (Dhib-Jalbut, Neurology, vol. 68, no. 22, supplement 3, pp. S13-S54, 2007; Fletcher et al., Clinical and Experimental Immunology, vol. 162, no. 1, pp. 1-11, 2010; Hemmer et al., Nature Reviews Neuroscience, vol. 3, no. 4, pp. 291-301, 2002). However, the symptoms and animal susceptibility of EAE depend on the types of immunizing antigens and strains or species of animals used. Not all myelin antigens work in every rodent strain, and different combinations may induce animal models reflecting different subtypes and clinical course of MS. H-2U mice, especially the PL/J strains, are highly susceptible to MBP-induced EAE. SJL mice are susceptible to PLP-induced EAE and result in a remitting-relapsing EAE course. However, the most commonly used strain is the C57BL/6(B6) mice, as many transgenic and knockout animals are maintained on this genetic background. The C57BL/6 mice are not susceptible to MBP-induced EAE; they develop symptoms only after immunization with MOG. They can exhibit either mild/transient or severe/chronic phages depending on dosage of myelin components and immunization times (Kuerten and Angelov, Annals of Anatomy, vol. 190, no. 1, pp. 1-15, 2008). For rat EAE, the most commonly used strain is the Lewis rats that are sensitive to both MBP and MOG-induced disease.

Theiler's murine encephalomyelitis virus-induced demyelinating disease (TMEV-IDD) is another inflammatory model of MS. Different from EAE, TMEV-IDD is initiated by virus infection. Responses from immune cells in this model, such as the cell types that react and the timing of reaction, may differ from EAE (Denic et al., Pathophysiology, vol. 18, no. 1, pp. 21-29, 2011; Chastain et al., Biochimica et Biophysica Acta, vol. 1812, no. 2, pp. 265-274, 2011).

Along similar lines, subcutaneous injection of BCG (bacillus Calmette-Guérin) has been shown to induce a delayed-type hypersensitivity (DTH) response accompanied by infiltration of macrophages and lymphocytes, the breakdown of the blood-brain barrier and immunoreactive myelin loss (Matyszak and Perry, Journal of Neuroimmunology, vol. 69, no. 1-2, pp. 141-149, 1996).

There are other useful animal models of MS that induce chemical injury, such as cuprizone, lysolecithin and ethidium bromide, and result in focal demyelination in the white matter. These models are valued for studying the mechanism of demyelination/remyelination (as remyelination is initiated upon termination of the chemical injury reagent), but they cannot account for the whole picture of MS, because they are devoid of a massive leukocyte infiltration (Chastain et al., Biochimica et Biophysica Acta, vol. 1812, no. 2, pp. 265-274, 2011; Torkildsen et al., Acta Neurologica Scandinavica, vol. 117, supplement 188, pp. 72-76, 2008; Blakemore and Franklin, Current Topics in Microbiology and Immunology, vol. 318, pp. 193-212, 2008).

To create lysolecithin animal model, demyelination was induced in Gli1-CreER; Rgfp mice by stereotaxic injection of 1 microliter 2% Lysolecithin in the Corpus Callosum. The brains were assessed by immunohistochemistry 2 weeks following the injection. The inventors observed labeled cells migrating to the demyelinated area and these cells also differentiated into CC1 expressing mature oligodendrocytes.

Other models of demyelination and remyelination that may prove useful to interrogate the effects of inhibiting Gli1 on remyelination include new genetic models to synchronously ablate oligodendroctyes in adult mice. This method relies on genetic expression of diptheria toxin in oligodendrocytes and results in massive demyelination, followed by a wave of remyelination (Traka et al, Brain, vol. 133, pp. 3017-3029, 2010). This model may also simulate autoimmune demyelination via development of a secondary, age-delayed demyelination.

All of these models have their limitations. EAE, even though it has the drawback that the disease onset is specifically due to a defined antigen presentation as opposed to MS, appears to relatively better reflect and recapitulate critical features and progressions of MS; therefore, most of the current mechanism studies and treatments for MS still mainly rely on EAE models (Steinman and Zamvil, Annals of Neurology, vol. 60, no. 1, pp. 12-21, 2006).

EAE mice model of MS will be thus used in the initial animal studies. Mice will be treated will Gli1 inhibitor (e.g., GANT61, initial concentration 5-10 mg/kg/day) during the induction period of EAE (i.e., during the administration of the immunogen [MOG peptide]) and for several weeks thereafter. Remyelination will be assessed by a combination of immunostaining for myelin proteins, cytochemistry (e.g., myelin black gold), electron microscopy, and by functional analysis assessing recovery of neurological function.

Example 4

Figure 7:
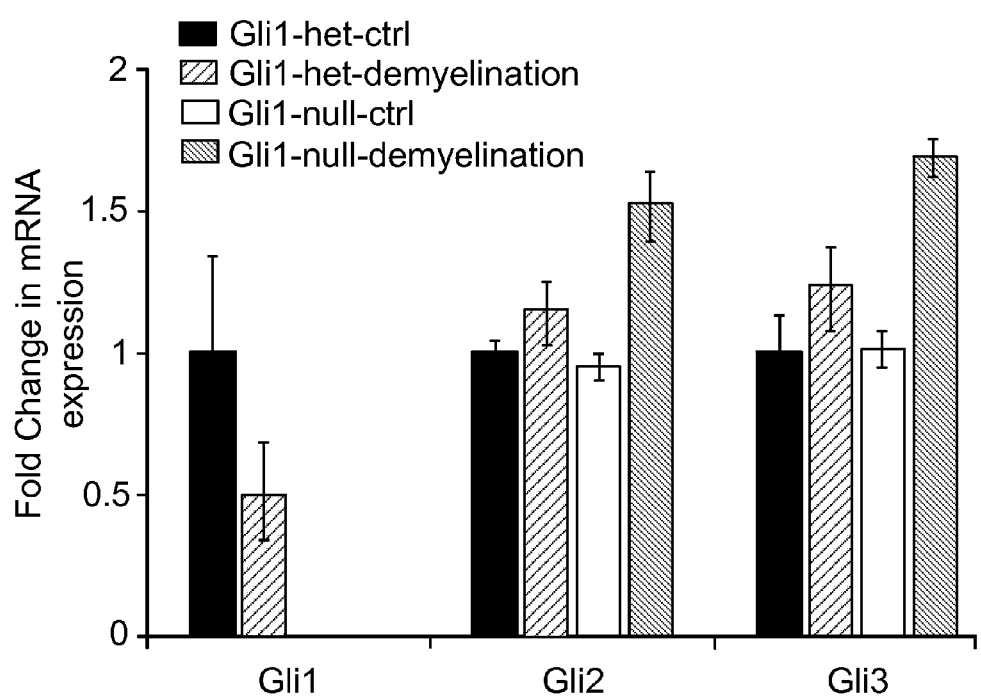
FIG. 7 is a graph showing the results of quantitative reverse-transcriptase PCR (QPCR) analysis of mRNA extracted from the corpus callosum (CC) of Gli1-heterozygous (Gli1-het) and Gli1-null mice on control diet as well as on cuprizone diet for 5 wks. QPCR analysis shows that mRNA levels of Gli2 and Gli3 are significantly increased upon demyelination in the Gli1-null mice.

Role of Gli2 and Gli3 in Gli1-Null Mice mRNA was extracted from the corpus callosum (CC) of Gli1-heterozygous (Gli1-het) and Gli1-null mice on control diet as well as on cuprizone diet for 5 wks. Quantitative reverse-transcriptase PCR (QPCR) analysis showed that mRNA levels of Gli2 and Gli3 are significantly increased upon demyelination in the Gli1-null mice (FIG. 7).

These results suggest that upregulation of Gli2 and Gli3 may be either responsible for the enhanced remyelination observed in Gli1-null mice or may further increase the remyelination in Gli-null mice. To confirm this genetically, mice were generated which are either heterozygous or null for Gli1 and have constitutively active Smo due to a point mutation W539L in the gene (SmoM2 mice from Jackson Laboratories) that can be conditionally activated by cre-lox recombination. Specifically, the Gli1$^{CreER/+}$ mice and Gli1$^{CreER/LacZ}$ mice were mated to SmoM2$^{c/c}$ mice and Gli1$^{CreER/+}$;SmoM2$^{c/c}$ (Gli1-het;SmoM2) and Gli1$^{CreER/LacZ}$;SmoM2$^{c/c}$ (Gli1-null;SmoM2) mice were obtained.

Demyelination was induced in Gli1-het;SmoM2 and Gli1-null;SmoM2 mice with cuprizone diet for 6 weeks and the cells were activated and/or labeled by i.p. injection of tamoxifen in the 5th week of cuprizone diet. The brains were analyzed by immunofluorescence after stopping cuprizone diet for 2 weeks to allow remyelination. Highest numbers of labeled cells were observed in the CC of Gli1-null;SmoM2 mice undergoing demyelination (FIG. 8).

Figure 8:
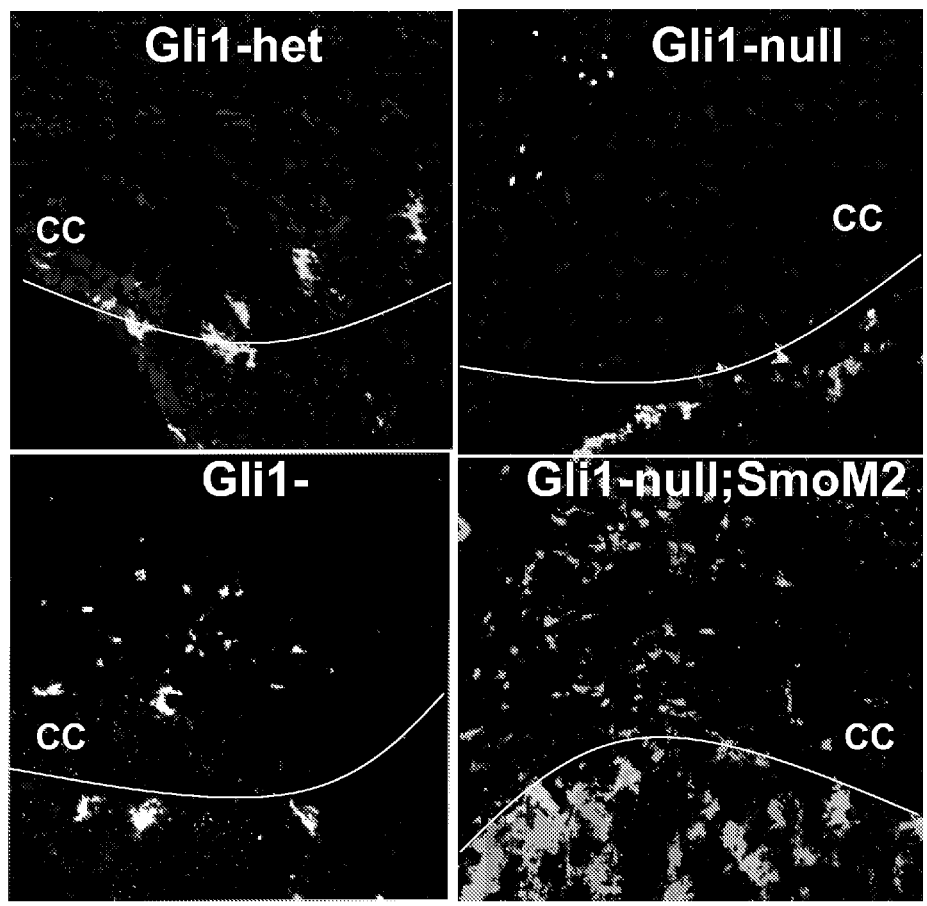
FIG. 8 shows immunofluorescence analysis of brains in Gli1-het;SmoM2 and Gli1-null;SmoM2 mice after demyelination was induced with cuprizone diet for 6 weeks and the cells were activated and/or labeled by i.p. injection of tamoxifen in the 5th week of cuprizone diet followed by stopping cuprizone diet for 2 weeks to allow remyelination.
Figure 9:
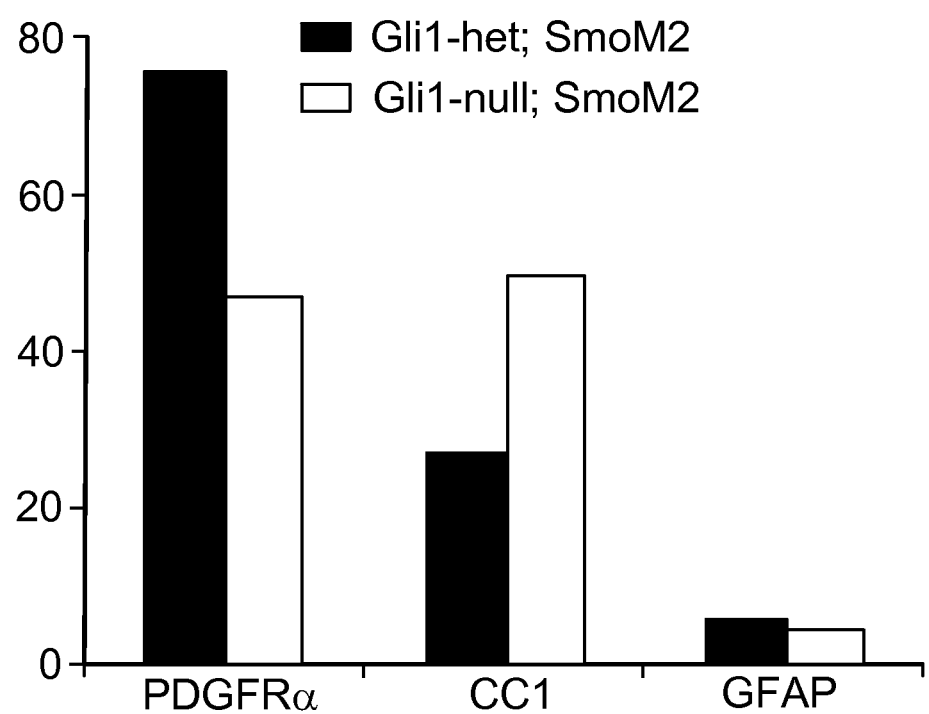
FIG. 9 shows quantitation of the results in FIG. 5 showing that Gli1-null;SmoM2 mice show enhanced differentiation of oligodendrocyte (OL) progenitors marked by expression of PDGFRα into mature OLs marked by expression of CC1. There was no change in numbers of astrocytes expressing GFAP. (Y axis shows percentage of GFP labeled cells co-expressing the markers).

As shown in FIG. 9, preliminary quantitation of the results in FIG. 8 showed that Gli1-null;SmoM2 mice show enhanced differentiation of oligodendrocyte (OL) progenitors marked by expression of PDGFRα into mature OLs marked by expression of CC1. There was no change in numbers of astrocytes expressing GFAP. (Y axis shows percentage of GFP labeled cells co-expressing the markers).

These results indicate that inhibition of Gli1 along with upregulation of Gli2 and Gli3 provide better remyelination and this could be used as a therapeutic strategy in demyelinating diseases.

REFERENCES

Ahn, S. & Joyner, A. L. In vivo analysis of quiescent adult neural stem cells responding to Sonic hedgehog. Nature 437, 894-897 (2005).

Ahn, S. & Joyner, A. L. Dynamic changes in the response of cells to positive hedgehog signaling during mouse limb patterning. Cell 118, 505-516 (2004).

Alvarez, J. I. et al. The Hedgehog pathway promotes blood-brain barrier integrity and CNS immune quiescence. Science 334, 1727-1731, doi:10.1126/science.1206936 (2011).

Amankulor, N. M. et al. Sonic hedgehog pathway activation is induced by acute brain injury and regulated by injury-related inflammation. The Journal of neuroscience: the official journal of the Society for Neuroscience 29, 1029910308, doi:10.1523/JNEUROSCI. 2500-09.2009 (2009).

Bai, C. B., Auerbach, W., Lee, J. S., Stephen, D. & Joyner, A. L. Gli2, but not Gli1, is required for initial Shh signaling and ectopic activation of the Shh pathway. Development 129, 4753-4761 (2002).

Balordi, F. & Fishell, G. Mosaic removal of hedgehog signaling in the adult SVZ reveals that the residual wild-type stem cells have a limited capacity for self-renewal. The Journal of Neuroscience: the official journal of the Society for Neuroscience 27, 14248-14259, doi:10.1523/JNEUROSCI. 4531-07.2007 (2007).

Bruce, C. C., Zhao, C., and Franklin, R. J. (2010) Remyelination—An effective means of neuroprotection. Horm Behav 57, 56-62.

Dubois-Dalcq, M., French-Constant, C., and Franklin, R. J. (2005). Enhancing central nervous system remyelination in multiple sclerosis. Neuron 48, 9-12.

Elsworth, S. & Howell, J. M. Variation in the response of mice to cuprizone. Research in veterinary science 14, 385-387 (1973).

Fancy S P, Harrington E P, Yuen T J, Silbereis J C, Zhao C, Baranzini S E, Bruce C C, Otero J J, Huang E J, Nusse R, Franklin R J, Rowitch D H (2011) Axin2 as regulatory and therapeutic target in newborn brain injury and remyelination. Nature Neuroscience 14:1009-1016.

Franklin, R. J. M. & ffrench-Constant, C. Remyelination in the CNS: from biology to therapy. Nat Rev Neurosci 9, 839-855 (2008).

Franklin, R. J., Gilson, J. M. & Blakemore, W. F. Local recruitment of remyelinating cells in the repair of demyelination in the central nervous system. Journal of neuroscience research 50, 337-344 (1997).

Garcia, A. D., Petrova, R., Eng, L. & Joyner, A. L. Sonic hedgehog regulates discrete populations of astrocytes in the adult mouse forebrain. The Journal of neuroscience: the official journal of the Society for Neuroscience 30, 13597-13608, doi:10.1523/JNEUROSCI. 0830-10.2010 (2010).

Gensert, J. M. & Goldman, J. E. Endogenous progenitors remyelinate demyelinated axons in the adult CNS. Neuron 19, 197-203 (1997).

Goldman, S. A., Nedergaard, M. & Windrem, M. S. Glial progenitor cell-based treatment and modeling of neurological disease. Science 338, 491-495, doi:10.1126/science.1218071 (2012).

Goldman, S. A., Schanz, S., and Windrem, M. S. (2008). Stem cell-based strategies for treating pediatric disorders of myelin. Hum Mol Genet. 17, R76-83.

Huang, J. K. & Franklin, R. J. Current status of myelin replacement therapies in multiple sclerosis. Progress in brain research 201, 219-231, doi:10.1016/B978-0-444-59544-7.00011-1 (2012).

Huang J K, Fancy S P, Zhao C, Rowitch D H, Ffrench-Constant C, Franklin R J (2011) Myelin regeneration in multiple sclerosis: targeting endogenous stem cells. Neurotherapeutics 8:650-658.

Huang J K, Jarjour A A, Nait Oumesmar B, Kerninon C, Williams A, Krezel W, Kagechika H, Bauer J, Zhao C, Evercooren A B, Chambon P, Ffrench-Constant C, Franklin R J (2011) Retinoid X receptor gamma signaling accelerates CNS remyelination. Nature Neuroscience 14:45-53.

Ihrie, R. A. et al. Persistent sonic hedgehog signaling in adult brain determines neural stem cell positional identity. Neuron 71, 250-262, doi:10.1016/j.neuron.2011.05.018 (2011).

Ingham, P. W. & McMahon, A. P. Hedgehog signaling in animal development: paradigms and principles. Genes Dev. 15, 3059-3087 (2001).

Jeong, J., Mao, J., Tenzen, T., Kottmann, A. H. & McMahon, A. P. Hedgehog signaling in the neural crest cells regulates the patterning and growth of facial primordia. Genes & development 18, 937-951, doi:10.1101/gad.1190304 (2004).

Kohama, S. G., Rosene, D. L., and Sherman, L. S. (2011). Age-related changes in human and non-human primate white matter: from myelination disturbances to cognitive decline. Age (Dordr).

Lauth, M., Bergstrom, A., Shimokawa, T. & Toftgard, R. Inhibition of GLI-mediated transcription and tumor cell growth by small-molecule antagonists. Proc Natl Acad Sci USA 104, 8455-8460, doi:10.1073/pnas.0609699104 (2007).

Loulier, K., Ruat, M. & Traiffort, E. Increase of proliferating oligodendroglial progenitors in the adult mouse brain upon Sonic hedgehog delivery in the lateral ventricle. J Neurochem 98, 530-542 (2006).

Matise, M. P., and Wang, H. (2011). Sonic hedgehog signaling in the developing CNS where it has been and where it is going. Curr Top Dev Biol 97, 75-117.

Matsushima, G. K. & Morell, P. The neurotoxicant, cuprizone, as a model to study demyelination and remyelination in the central nervous system. Brain Pathol 11, 107-116 (2001).

Menn, B., Garcia-Verdugo, J. M., Yaschine, C., Gonzalez-Perez, O., Rowitch, D., and Alvarez-Buylla, A. (2006). Origin of oligodendrocytes in the subventricular zone of the adult brain. J Neurosci 26, 7907-7918.

Mullard, A. (2011). Success of immunomodulators in MS shifts discovery focus to neuroprotection. Nat Rev Drug Discov 10, 885-887.

Nait-Oumesmar, B. et al. Activation of the subventricular zone in multiple sclerosis: evidence for early glial progenitors. Proc Natl Acad Sci USA 104, 4694-4699 (2007).

Nave, K. A. & Trapp, B. D. Axon-glial signaling and the glial support of axon function. Annu Rev Neurosci 31, 535-561, doi:10.1146/annurev.neuro.30.051606.094309 (2008).

Nery, S., Wichterle, H. & Fishell, G. Sonic hedgehog contributes to oligodendrocyte specification in the mammalian forebrain. Development 128, 527-540 (2001).

Palma, V. & Ruiz i Altaba, A. Hedgehog-GLI signaling regulates the behavior of cells with stem cell properties in the developing neocortex. Development 131, 337-345 (2004).

Picard-Riera, N., Decker, L., Delarasse, C., Goude, K., Nait-Oumesmar, B., Liblau, R., Pham-Dinh, D., and Evercooren, A. B. (2002). Experimental autoimmune encephalomyelitis mobilizes neural progenitors from the subventricular zone to undergo oligodendrogenesis in adult mice. Proc Natl Acad Sci USA 99, 13211-13216.

Prineas, J. W., Barnard, R. O., Kwon, E. E., Sharer, L. R., and Cho, E. S. (1993). Multiple sclerosis: remyelination of nascent lesions. Ann Neurol 33, 137-151.

Rowitch, D. H. Sonic hedgehog regulates proliferation and inhibits differentiation of CNS precursor cells. J. Neurosci. 19, 8954-8965 (1999).

Scolding, N. et al. Oligodendrocyte progenitors are present in the normal adult human CNS and in the lesions of multiple sclerosis. Brain 121 (Pt 12), 2221-2228 (1998).

Seifert, T., Bauer, J., Weissert, R., Fazekas, F. & Storch, M. K. Differential expression of sonic hedgehog immunoreactivity during lesion evolution in autoimmune encephalomyelitis. J Neuropathol Exp Neurol 64, 404-411 (2005).

Smith, E. J., Blakemore, W. F., and McDonald, W. I. (1979). Central remyelination restores secure conduction. Nature 280, 395-396.

Sousa, V. H., Miyoshi, G., Hjerling-Leffler, J., Karayannis, T. & Fishell, G. Characterization of Nkx6-2-derived neocortical interneuron lineages. Cerebral cortex 19 Suppl 1, i1-10, doi:10.1093/cercor/bhp038 (2009).

Tekki-Kessaris, N. Hedgehog-dependent oligodendrocyte lineage specification in the telencephalon. Development 128, 2545-2554 (2001).

Wang, Y., Imitola, J., Rasmussen, S., O'Connor, K. C. & Khoury, S. J. Paradoxical dysregulation of the neural stem cell pathway sonic hedgehog-Gli1 in autoimmune encephalomyelitis and multiple sclerosis. Ann Neurol 64, 417-427, doi:10.1002/ana.21457 (2008).

Zhao, C., Fancy, S. P., Kotter, M. R., Li, W. W., and Franklin, R. J. (2005). Mechanisms of CNS remyelination—the key to therapeutic advances. J Neurol Sci 233, 87-91.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All patents, applications, publications, test methods, literature, and other materials cited herein are hereby incorporated by reference in their entirety as if physically present in this specification.

The invention claimed is:

1. A method for enhancing remeyelination in a subject in need thereof comprising administering to said subject an effective amount of a Gli1 inhibitor.

2. The method of claim 1, wherein the subject has a neurological disorder characterized by myelin loss or myelin deficiency.

3. A method for enhancing neuroprotection of a central nervous system (CNS) or peripheral nervous system (PNS) neuron in a subject in need thereof comprising administering to said subject an effective amount of a Gli1 inhibitor.

4. The method of claim 3, wherein the subject has a neurological disorder characterized by myelin loss or myelin deficiency.

5. A method for treating a neurological disorder characterized by myelin loss or myelin deficiency in a subject in need thereof comprising administering to said subject a therapeutically effective amount of a Gli1 inhibitor.

6. The method of claim 2, wherein the neurological disorder is selected from the group consisting of multiple sclerosis (MS), Central Pontine Myelinolysis, Acute Disseminated Encephalomyelitis, Progressive Multifocal Leukoencephalopathy, Subacute Sclerosing Panencephalitis, Post-infectious Encephalomyelitis, Chronic Inflammatory Demyelinating Polyneuropathy, Devic's Disease, Balo's Concentric Sclerosis, the leukodystrophies, optic neuritis, transverse myelitis, cerebral palsy, spinal cord injury, age-associated myelin deficiency, and acquired and inherited neuropathies in the peripheral nervous system.

7. The method of claim 2, wherein the neurological disorder is multiple sclerosis (MS).

8. The method of claim 1, wherein the Gli1 inhibitor is GANT61 or GANT58.

9. The method of claim 1, wherein the Gli1 inhibitor is selected from the group consisting of genistein, epigallocatechin gallate (EGCG), zerumbone, zerumbone epoxide, staurosporinone, 6-hydroxystaurosporinone, arcyriaflavin C, 5,6-dihydroxyarcyriaflavin A, physalin F, and physalin B.

10. The method of claim 1, wherein the Gli1 inhibitor is selected from the group consisting of NMDA298-1, JK184, and HPI-1 through HPI-4.

11. The method of claim 1, wherein the Gli1 inhibitor is siRNA.

12. The method of claim 1, wherein the Gli1 inhibitor is a compound of formula (1):

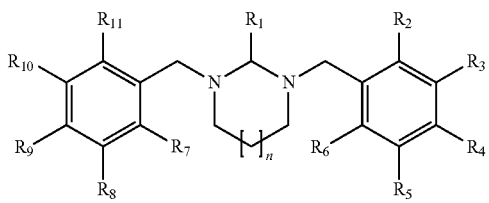

(1)

wherein n is 0, 1, or 2;

$R_1$ is $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; and each of $R_2$, $R_3$, $R_4$, $R_5$, $R_6$, $R_7$, $R_8$, $R_9$, $R_{10}$, and $R_{11}$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, halo, $OR_a$, $COOR_a$, $OC(O)R_a$, $C(O)R_a$, $C(O)NR_aR_b$, or $NR_aR_b$, in which each of $R_a$ and $R_b$, independently, is H, $C_1$-$C_{10}$ alkyl, $C_3$-$C_{20}$ cycloalkyl, $C_1$-$C_{20}$ heterocycloalkyl, aryl, or heteroaryl.

13. The method of claim 12, wherein n is 1.

14. The method of claim 13, wherein $R_1$ is heteroaryl.

15. The method of claim 14, wherein $R_1$ is 4-pyridyl.

16. The method of claim 15, wherein each of $R_2$ and $R_{11}$ is $NR_aR_b$ and each of $R_3$, $R_4$, $R_5$, $R_6$, $R_7$, $R_8$, $R_9$, and $R_{10}$ is H.

17. The method of claim 16, wherein each of $R_2$ and $R_{11}$ is $N(CH_3)_2$.

18. The method of claim 1, wherein the Gli1 inhibitor is selected from the group consisting of

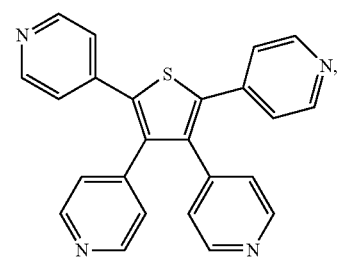

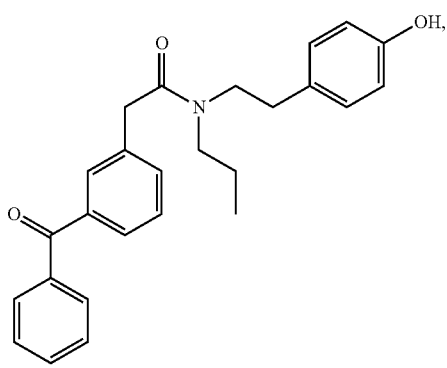

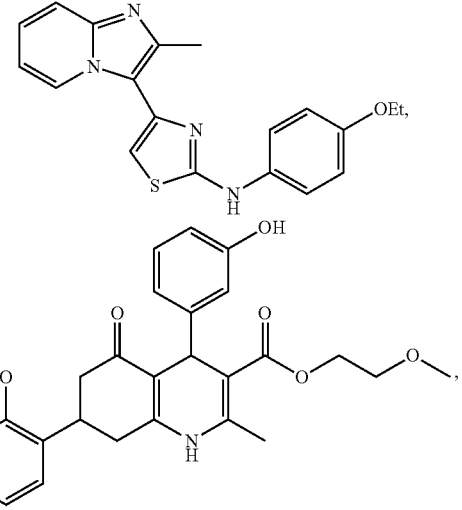

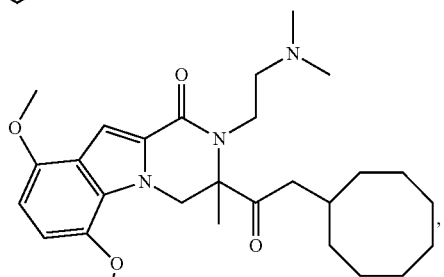

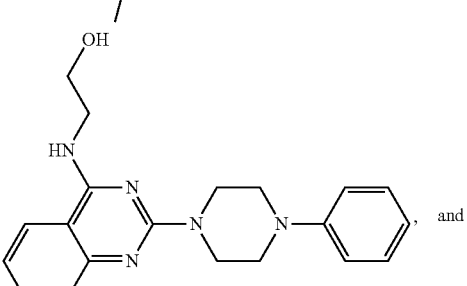

, and

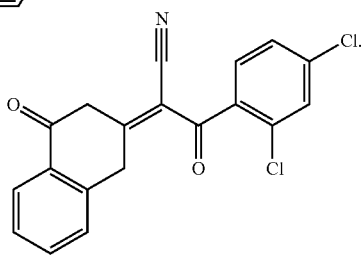

19. The method of claim 1, further comprising administering at least one additional agent that limits demyelination or enhances remyelination.

20. The method of claim 1, further comprising administering at least one agent which causes upregulation and/or increases activity of Gli2 and/or Gli3.

21. The method of claim 1, further comprising administering at least one agonist of smoothened (Smo).

22. A method for increasing recruitment of Gli1-expressing stem cells to site(s) of myelin loss or myelin deficiency and/or increasing their differentiation into mature oligodendrocytes in a subject in need thereof comprising administering to said subject an effective amount of a Gli1 inhibitor.

* * * * *

SEQUENCE LISTING

```
<160> NUMBER OF SEQ ID NOS: 6

<210> SEQ ID NO 1
<211> LENGTH: 9
<212> TYPE: DNA
<213> ORGANISM: Artificial Sequence
<220> FEATURE:
<223> OTHER INFORMATION: consensus GLI-selective sequence

<400> SEQUENCE: 1 gaccaccca                                                             9

<210> SEQ ID NO 2
<211> LENGTH: 21
<212> TYPE: DNA
<213> ORGANISM: Artificial Sequence
<220> FEATURE:
<223> OTHER INFORMATION: siRNA

<400> SEQUENCE: 2
```

-continued

```
gucauuauca aauuucucct t                                      21

<210> SEQ ID NO 3
<211> LENGTH: 21
<212> TYPE: DNA
<213> ORGANISM: Artificial Sequence
<220> FEATURE:
<223> OTHER INFORMATION: siRNA

<400> SEQUENCE: 3
agaagaaaag agugggccct t                                      21

<210> SEQ ID NO 4
<211> LENGTH: 21
<212> TYPE: DNA
<213> ORGANISM: Artificial Sequence
<220> FEATURE:
<223> OTHER INFORMATION: siRNA

<400> SEQUENCE: 4
uccgguguuu ucuucaucct t                                      21

<210> SEQ ID NO 5
<211> LENGTH: 21
<212> TYPE: DNA
<213> ORGANISM: Artificial Sequence
<220> FEATURE:
<223> OTHER INFORMATION: siRNA

<400> SEQUENCE: 5
gagaucuucc cuucauacct t                                      21

<210> SEQ ID NO 6
<211> LENGTH: 21
<212> TYPE: RNA
<213> ORGANISM: Artificial Sequence
<220> FEATURE:
<223> OTHER INFORMATION: siRNA

<400> SEQUENCE: 6
aacuccacag gcauacagga u                                      21
```